United States Patent
Raskin et al.

(10) Patent No.: US 9,480,235 B1
(45) Date of Patent: Nov. 1, 2016

(54) RED LETTUCES WITH INCREASED ANTHOCYANINS, POLYPHENOLS, AND OXYGEN RADICAL ABSORPTION CAPACITY

(71) Applicant: Rutgers, The State University of New Jersey, New Brunswick, NJ (US)

(72) Inventors: Ilya Raskin, Manalapan, NJ (US); Diana Cheng, Highland Park, NJ (US); Natalia Pogrebnyak, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 685 days.

(21) Appl. No.: 13/901,804

(22) Filed: May 24, 2013

Related U.S. Application Data

(60) Provisional application No. 61/651,122, filed on May 24, 2012.

(51) Int. Cl.
| | | |
|---|---|---|
| C12N 15/01 | (2006.01) |
| A01H 4/00 | (2006.01) |
| A01H 5/12 | (2006.01) |
| A61K 36/28 | (2006.01) |
| A61P 3/10 | (2006.01) |
| C12N 15/82 | (2006.01) |

(52) U.S. Cl.
CPC ............... *A01H 5/12* (2013.01); *A61K 36/28* (2013.01); *C12N 15/01* (2013.01); *C12N 15/8241* (2013.01)

(58) Field of Classification Search
None
See application file for complete search history.

(56) References Cited

U.S. PATENT DOCUMENTS 7,126,045 B2    10/2006   Knerr
2011/0083225 A1*  4/2011   Knerr ................. A01H 5/12
                                                    800/265

OTHER PUBLICATIONS

Kaeppler et al (PMB, 43: 179-188, 2000).*
Lai et al (Biotechnology and Bioengineering 86(6): 622-627, 2004).*
Llorach et al (Food Chemistry, 2008, 108(3): 1028-1038).*

* cited by examiner

*Primary Examiner* — Elizabeth McElwain
*Assistant Examiner* — Stephen Uyeno
(74) *Attorney, Agent, or Firm* — Klarquist Sparkman, LLP

(57) ABSTRACT

Provided herein are several improved lettuce varieties, having increased anthocyanin and polyphenol content, and increased oxygen radical absorption capacity, as compared to other known varieties of lettuce. Also provided are parts of such new lettuces, such as leaves, heads, seeds, tissue cultures, and extracts generated from such varieties. The disclosure also provides methods of using the new lettuces and parts thereof, for example to reduce blood glucose levels.

26 Claims, 5 Drawing Sheets
(5 of 5 Drawing Sheet(s) Filed in Color)

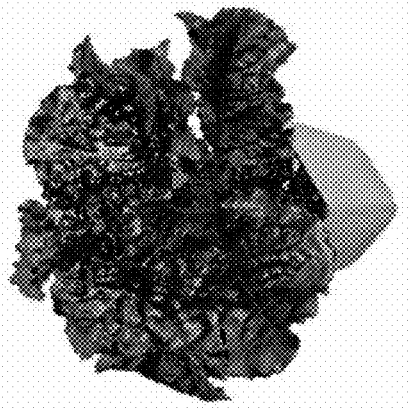
FIG. 6B
FIG. 6C
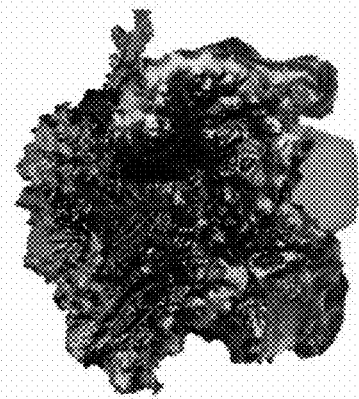
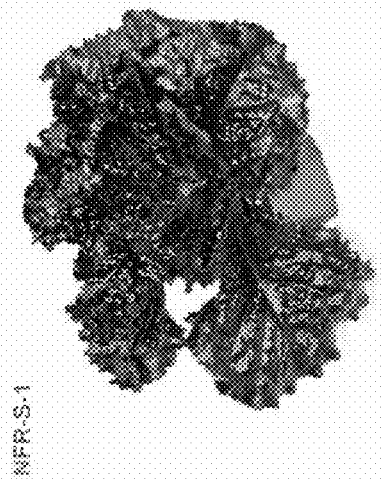
FIG. 6A
FIG. 6D
FIG. 6G
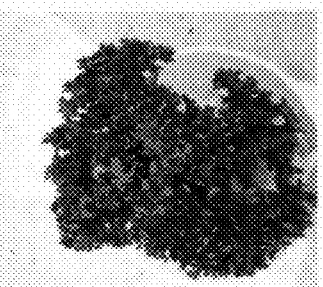
FIG. 6F
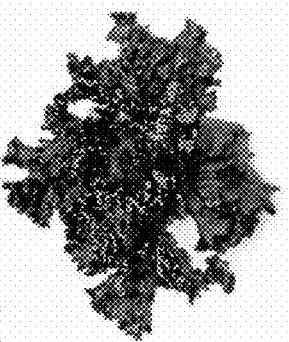
FIG. 6E
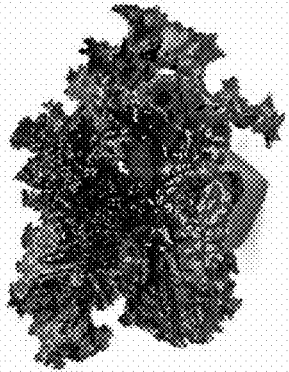

RED LETTUCES WITH INCREASED ANTHOCYANINS, POLYPHENOLS, AND OXYGEN RADICAL ABSORPTION CAPACITY

CROSS-REFERENCE TO RELATED APPLICATION

This application claims priority to U.S. Provisional Application No. 61/651,122 filed May 24, 2012, herein incorporated by reference.

FIELD

This application relates to several new red lettuce varieties having high anthocyanin and polyphenol content and increased oxygen radical absorption capacity, extracts from the variety, and uses of the lettuce and its extracts, for example to reduce blood glucose levels.

BACKGROUND

There is an increasing demand by consumers for nutritious foods that improve physical performance, reduce risks of disease, and increase life span. Researchers and food manufacturers are interested in increasing polyphenols and particularly anthocyanins in foods, due to the antioxidant properties of these compounds and their role in the prevention of various diseases, such as many types of cancer, cardiovascular and neurodegenerative diseases (1-5). In addition, anthocyanins have anti-inflammatory activity, improve visual acuity, modulate the immune response and hinder obesity and diabetes (6-8).

Since these health-promoting effects depend on relatively high level of anthocyanins, there is a strong need to increase their amounts in human diet. Blueberries are one of the richest sources of anthocyanins and are highly recommended for human consumption (10). However, despite its beneficial properties, blueberry consumption per capita is still low compared to other types of fresh fruits and vegetables. In addition, blueberries contain high amounts of sugar, which may not be desirable for many individuals. Thus, there is a need to develop other plants with increased anthocyanins and total polyphenol content, with less sugar, that could gain wide popularity among public, and can become part of everyday food intake.

Lettuce (*Latuca sativa* L) is widely used in salads and sandwiches, and is an important component in human diet and nutrition. Recently, lettuce was the second most consumed fresh vegetable in the USA behind potatoes (9). Red lettuce cultivars could be relevant as dietary sources of natural antioxidant compounds, anthocyanins and other polyphenols. Anthocyanins accumulate in cell vacuoles of lettuce and are responsible for pigmentation from red to dark purple color. However, most of red lettuce cultivars, especially head forming types, are not typically red throughout the leaves. In many cases, they are only red along the leaf edges or speckled with red. The synthesis of anthocyanins in lettuce is induced by light, especially UV-radiation (16-17); therefore, the red color is expressed in those parts of plants that are exposed to daylight and UV-radiation.

Recent studies have shown that amounts of polyphenols and anthocyanins produced in different red lettuce cultivars under various light intensities, growth conditions and temperature were significantly lower than in blueberry (11-15).

SUMMARY

The present disclosure provides lettuce cultivars with increased amounts of anthocyanins, total polyphenols and greater antioxidant capacity, compared to existing cultivars. Also provided herein are methods of producing such cultivars, for example using somaclonal variations in plant tissue culture and protoplast culture conditions as well as induced mutagenesis technologies. The disclosure also provides extracts from such lettuce cultivars, methods of making such extracts, and methods of using such extracts, for example to reduce inflammation, improve visual acuity, modulate the immune response, reduce obesity and diabetes, reduce blood glucose levels, or combinations thereof.

Deposits of the new lettuce varieties will be made with the American Type Culture Collection (ATCC), 10801 University Blvd., Manassas, Va., 20110. The date of deposit was Oct. 30, 2013. The deposits are intended to meet all of the requirements of 37 C.F.R. §§1.801-1.809. The accession number for those deposited seeds of the new lettuce varieties disclosed herein are ATCC Accession Nos. PTA-120680, PTA-120681 and PTA-120682. Access to these deposits will be available during the pendency of the application to the Commissioner of Patents and Trademarks and persons determined by the Commissioner to be entitled thereto upon request. The deposit will be maintained in the depository for a period of 30 years, or 5 years after the last request, or for the effective life of the patent, whichever is longer, and will be replaced if necessary during that period. Applicants do not waive any infringement of rights granted under this patent or under the Plant Variety Protection Act (7 U.S.C. 2321 et seq.).

In one embodiment, the disclosure provides lettuce seed deposited as ATCC Accession No. PTA-120680, PTA-120681 or PTA-120682, as well as lettuce seed mixtures containing such seeds.

The disclosure provides lettuce plants having, consisting essentially of, or consisting of the morphological and physiological characteristics of the new lettuce varieties provided herein, such as the characteristics noted in Tables 3-5, for example increased anthocyanins, phenolics, and/or oxygen radical absorption capacity as compared to other varieties. In one example, the new lettuce varieties have at least 5 mg/g fresh weight (FW) phenolics (measured in gallic acid equivalents), at least 0.5 mg/g FW anthocyanins (measured in cyanidin-3-glucoside equivalents), and at least 100, at least 200, at least 210, at least 220, at least 230, at least 240, at least 250, at least 260, at least 270, or at least 300 μmol/g FW oxygen radical absorption capacity (measured in trolox equivalents). In one example, the new lettuce varieties have at least 10 mg/g dry weight (DW) chlorogenic acid (such as at least 15, at least 20, at least 21, at least 22, at least 23, at least 24, at least 25, or at least 26 mg/g DW chlorogenic acid), at least 4 mg/g DW quercetin 3 glucoside (such as at least 4, at least 5, at least 6, at least 7, at least 8, at least 8.5, at least 9, or at least 10 mg/g DW dicaffeoylquinic acid), at least 12 mg/g DW quercetin malonylglucoside (such as at least 15, at least 20, at least 25, at least 26, at least 27, at least 28, at least 29, at least 30, or at least 31 mg/g DW quercetin malonylglucoside), at least 7 mg/g DW cyanidin malonylglucoside (such as at least 10, at least 12, at least 15, at least 15.5, at least 16, at least 17, at least 18, at last 19, or at least 20 mg/g DW cyanidin malonylglucoside), or combinations thereof. Also provided are seeds of such plants, progeny of such plants, parts of such plants (such as leaves, pollen, ovules and cells), and tissue cultures generated from the cells of such plants. In one example, the disclosure provides lettuce plants having the genotype of one of the new varieties disclosed herein. For example, the disclosure provides plants produced by growing the seed of the new lettuce varieties disclosed herein.

The disclosure provides a tissue culture of regenerable cells of the new lettuce varieties, as well as plants regenerated therefrom. Such regenerated lettuce plants can include, consist essentially of, or consist of the physiological and morphological characteristics of a plant grown from the seed of the new lettuce varieties disclosed herein. Exemplary regenerable cells include but are not limited to those from protoplasts or cells, such as those from leaf, stem, protoplast, pollen, ovule, embryo, cotyledon, hypocotyl, meristematic cell, root, root tip, pistil, anther, flower, petal, seed, shoot, stein, or petiole of the new lettuce varieties provided herein.

Methods of producing lettuce seed from the new lettuce plants provided herein are provided. In some examples such methods include crossing a new lettuce variety provided herein with itself or a second lettuce plant and harvesting a resulting lettuce seed. In some examples, the second lettuce plant has a desirable trait, which is introduced into plants and seeds resulting from such a cross. For example, the second plant can be transgenic, wherein the transgene confers the desirable trait. Seeds produced by such methods, including $F_1$ hybrid seeds, as well as lettuce plants or parts thereof produced by growing such a seed, are provided. In some examples, the method of crossing includes planting seeds of a new lettuce variety provided herein, cultivating lettuce plants resulting from the seeds until the plants bear flowers, allowing fertilization of the flowers of the plants; and harvesting seeds produced from the plants.

Methods are provided for producing a plant of a new lettuce variety provided herein that has one or more added desired agronomic traits, as well as plants and seeds generated from such methods. In one example, such a method provides a lettuce plant having a single locus conversion of a new lettuce variety provided herein, wherein the lettuce plant includes or expresses the physiological and morphological characteristics of the new lettuce varieties provided herein (such as those shown in Table 3). In some embodiments, the single locus conversion can include a dominant or recessive allele. Such methods can include introducing one or more transgenes that confer one or more desired traits into a plant of one of new lettuce varieties provided herein. A transgenic or non-transgenic single locus conversion can also be introduced by backcrossing. Exemplary desired traits include herbicide tolerance or resistance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination; abiotic stress tolerance (such as tolerance to drought, heat, cold, low or high soil pH level, and/or salt), modified anthocyanins characteristics, modified antioxidant characteristics, modified phenolics characteristics, or other desired qualities.

Methods of introducing a single locus conversion (such as a desired trait) into one or more of the new lettuce varieties disclosed herein are provided. In some examples the methods include (a) crossing a plant of one of the new lettuce varieties disclosed herein with a second plant having one or more desired traits to produce $F_1$ progeny plants; (b) selecting $F_1$ progeny plants that have the desired trait to produce selected $F_1$ progeny plants; (c) crossing the selected progeny plants with at least a first plant of variety of one of the new lettuce varieties disclosed herein to produce backcross progeny plants; (d) selecting backcross progeny plants that have the desired trait and physiological and morphological characteristics of one of the new lettuce varieties disclosed herein to produce selected backcross progeny plants; and (e) repeating steps (c) and (d) one or more times in succession to produce selected second or higher backcross progeny plants that comprise the desired trait and the physiological and morphological characteristics of one of the new lettuce varieties disclosed herein when grown in the same environmental conditions. In some embodiments, the single locus confers a desirable trait, such herbicide tolerance or resistance, drought tolerance, heat tolerance, low or high soil pH level tolerance, salt tolerance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination, abiotic stress tolerance (such as tolerance to drought, heat, low or high soil pH level, and/or salt), modified anthocyanins characteristics, modified antioxidant characteristics, or modified phenolics characteristics. In some examples, the single locus confers the ability to synthesize a protein encoded by a gene located within the single locus.

Methods of producing a lettuce plant derived from a new lettuce variety provided herein, such as an inbred lettuce plant, are provided. In particular examples the method includes a) preparing a progeny plant derived from a new lettuce variety provided herein, by crossing a plant of a new lettuce variety provided herein with a lettuce plant of a second variety; and b) crossing the progeny plant with itself or a second plant to produce a progeny plant of a subsequent generation which is derived from a plant of a new lettuce variety provided herein. In some embodiments, the method further includes (c) growing a progeny plant of a subsequent generation from said seed and crossing the progeny plant of a subsequent generation with itself or a second plant; and (d) repeating steps (b) and (c) for at least 2 additional generations (such as at least 3, at least 5, or at least 10 additional generations) with sufficient inbreeding to produce an inbred lettuce plant derived from a new lettuce variety provided herein. In other examples, the method includes (a) crossing a lettuce plant derived from a new lettuce variety provided herein with itself or another lettuce plant to yield additional lettuce variety progeny lettuce seed derived from a new lettuce variety provided herein; (b) growing the progeny lettuce seed of (a) under plant growth conditions, to yield additional lettuce plants derived from a new lettuce variety provided herein; and (c) repeating the crossing and growing steps of (a) and (b) from 0 to 7 times (such as 0 to 4 or 1 to 5 times) to generate further lettuce plants derived from a new lettuce variety provided herein.

Methods are provided for developing a new lettuce plant using a new lettuce variety provided herein. For example, the methods can include using plants or parts of the new lettuce varieties provided herein as a source of breeding material in plant breeding techniques, such as recurrent selection, mass selection, bulk selection, backcrossing, pedigree breeding, genetic marker-assisted selection and genetic transformation. In some examples, a plant of a new lettuce variety provided herein is used as the male or female parent.

The disclosure provides a first generation ($F_1$) hybrid lettuce seed produced by crossing a plant of a new lettuce variety provided herein to a second lettuce plant. Also provided are the $F_1$ hybrid lettuce plants grown from the hybrid seed produced by crossing a new lettuce variety provided herein to a second lettuce plant. In some embodiments, the $F_1$ hybrid lettuce plant is grown from the hybrid seed produced by crossing a new lettuce variety provided herein to a second lettuce plant. In specific examples, provided is a seed of an $F_1$ hybrid plant produced with a new lettuce variety provided herein as one parent, the second generation ($F_2$) hybrid lettuce plant grown from the seed of the $F_1$ hybrid plant, and the seeds of the $F_2$ hybrid plant.

Methods of producing hybrid lettuce seeds are also provided. In one example the method includes crossing a new lettuce variety provided herein to a second, distinct lettuce plant which is nonisogenic to the new lettuce variety provided herein. In some examples, the method includes cultivating lettuce plants grown from seeds of a new lettuce variety provided herein and cultivating lettuce plants grown from seeds of a second, distinct lettuce plant, until the plants bear flowers. A flower on one of the two plants is cross pollinated with the pollen of the other plant, and the seeds resulting from such a cross are harvested.

The disclosure also provides lettuce plants and parts thereof produced by any of the methods disclosed herein. Thus, provided herein are plants of the new lettuce varieties provided herein that further include a single locus conversion, such as a desired trait, for example produced by backcrossing or genetic transformation. In some embodiments, the lettuce plants produced by the disclosed methods includes at least two, at least three, at least four, at least five, or at least 10 of the traits of a new lettuce variety as described herein. In some embodiments, the lettuce plants produced by the disclosed methods includes at least two, at least three, at least four, at least five, or at least 10 of the traits of the new lettuce varieties provided herein (see Table 3), such as increased anthocyanins, phenolics, and/or oxygen radical absorption capacity as described herein.

Methods are provided for producing and using an extract from the new lettuce varieties provided herein. For example, such an extract can be used to reduce fasting blood glucose levels, for example in a subject having type 2 diabetes.

Also provided herein is packaging material containing plant parts of one or more lettuce varieties provided herein. Such packaging material includes but is not limited to boxes, plastic bags, or other containers routinely used for lettuces. For example, the disclosure provides packages of lettuce or salad mixes (such as bags containing lettuce or lettuce leaves), which include leaves of one or more of the new varieties provided herein. The leaves of one or more of the new varieties provided herein may be combined with lettuce plant parts of other plant varieties.

Methods of regenerating a lettuce plant are provided. In some examples the method includes culturing lettuce cotyledons or young leaves in the presence of at least 0.1 mg/l 6-benzylaminopurine (BAP), at least 0.05 mg/l zeatin, and at least 0.02 mg/l naphthaleneacetic acid (NAA) thereby regenerating lettuce shoots.

Also provided are methods of generating and selecting lettuce plants having increased anthocyanins, phenolics, and/or oxygen radical absorption capacity, such as those having at least 1.1 mg/g FW anthocyanins. In some examples the method includes culturing either: lettuce cotyledons or young leaves in the presence of at least 0.1 mg/l 6-benzylaminopurine (BAP), at least 0.05 mg/l zeatin and at least 0.02 mg/l naphthaleneacetic acid (NAA); callus cultures or cell suspension in R9 medium comprising at least 0.1 mg/l BAP and at least 0.1 mg zeatin; or protoplasts in MS medium comprising at least 0.1 mg/l BAP and at least 0.01 mg NAA. The method can further include growing the lettuce cotyledons, young leaves, callus cultures or cell suspension, or protoplasts in the presence of blue and UV light (e.g., about 10 to 450 nm) to produce shoots and selecting shoots that are most red/purple in color. In some examples, the method can further include cutting the most red/purple shoots or segments of shoots into pieces and placing again on regeneration medium. After several rounds of regeneration and selection, the most dark red/purple variants are selected.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-6G are digital images showing lettuce F1 lines. (A) cv. Red Grand Rapids Firecracker line NFR S-1 produced from leaves after several regeneration cycles; (B) cv. Red Grand Rapids Firecracker line NFR S-4 produced from leaves after several regeneration cycles; (C) cv. Red Grand Rapids Firecracker line NFR S-6 produced from callus after several regeneration cycles; (D) cv. Red Grand Rapids Blackhawk NBR S-9, produced from callus after several regeneration cycles; (E) cv. Red Grand Rapids Blackhawk NBR S-16, produced from leaves after several regeneration cycles; (F) cv. Dark Red Lollo Rossa S-21-1 (NRR-S-21-1), produced after mutagenesis with EMS; and (G) cv. Red Romaine Annapolis line S-13, produced from callus.

DETAILED DESCRIPTION

Figure 1:
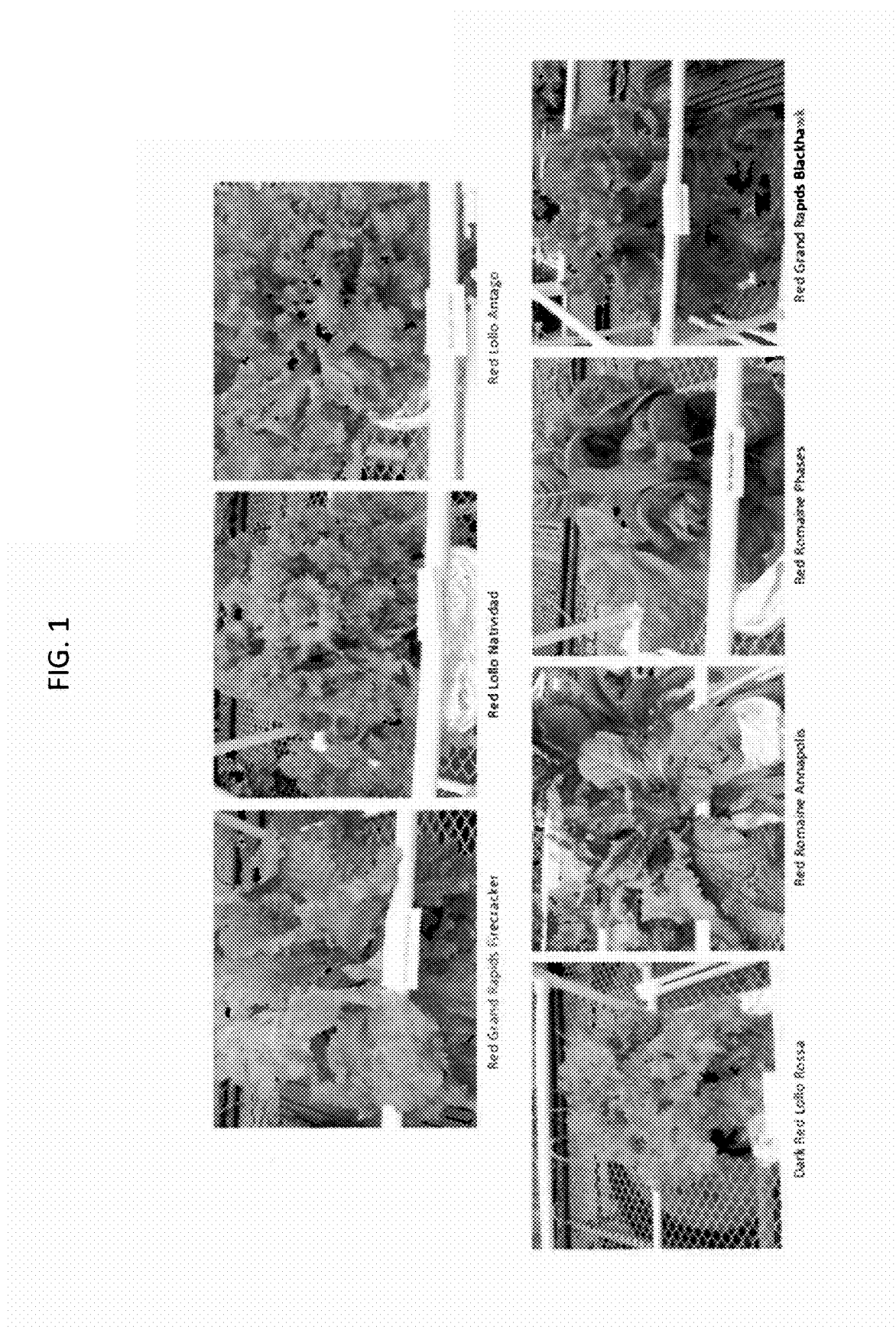
FIG. 1 is a digital image showing the original lettuce cultivars growing in a greenhouse.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Anthocyanins: Water-soluble, vacuolar pigments that are that may appear red, purple, or blue depending on the pH. Anthocyanins belong to a parent class of molecules called flavonoids, which can be synthesized via the phenylpropanoid pathway. Anthocyanins can occur in all tissues of higher plants, including leaves, stems, roots, flowers, and fruits. Exemplary anthocyanins include aurantinidin, cyanidin, delphinidin, europinidin, luteolinidin, malvidin, peonidin, petunidin and rosinidin.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first generation progeny of the cross of two nonisogenic plants.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Plant: Includes reference to an immature or mature whole plant, including a plant from which seed, roots or leaves have been removed. Seed or embryo that will produce the plant is also considered to be the plant.

Plant parts. Includes protoplasts, leaves, stems, roots, root tips, anthers, pistils, seed, embryo, pollen, ovules, cotyledon, hypocotyl, flower, shoot, tissue, petiole, cells, meristematic cells and the like. Includes plant cells of a tissue culture from which lettuce plants can be regenerated.

Polyphenols: Organic chemicals that include more than one phenol structural units. Polyphenols commonly found in lettuce include anthocyanins, chlorogenic acid, dicaffeoylquinic acid and quercetin.

Progeny. Offspring; descendants.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a lettuce variety are recovered in addition to the characteristics of the single locus transferred into the variety via the backcrossing technique.

Subject: Includes mammals, such as human and veterinary subjects. In one example a subject is one having type II diabetes.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a lettuce plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Lettuces with Increased Anthocyanins and Polyphenols

Plant tissue culture has been exploited to create genetic variability towards improvement of the crop plant. The past 30 years of research on plant tissue culture, regenerated plants, and their progeny have produced a rich array of genetic variants for many plants. Somaclonal variation (28) can provide a way for producing desirable characteristics in important crops. Mutagenic treatments can additionally enhance mutation frequency several fold. As shown herein, tissue culture technologies and mutagenesis were used to develop new lettuce cultivars with increased anthocyanin content.

Successful and efficient production of somaclonal and mutant lines is dependent on the regeneration capacity of plant genotypes. Despite a variety of tissue culture methods developed for lettuce (21, 22, 29, 30), most can only be used for particular cultivars. Additionally, in most cases, only cotyledon explants have been used for plant regeneration. It was previously reported that lettuce is highly genotype-dependent, both in regeneration capacity and callus induction (21-22). The first step herein was to develop efficient regeneration systems, including callus induction and cell suspension technologies for lettuce. A rapid and reproducible regeneration system for several lettuce cultivars belonging to leaf and Romaine types is provided herein. Compared to other methods described for lettuce, the disclosed system allows for the production of regenerants not only from cotyledons but also from leaves. This is the first report of regeneration, callus induction, cell suspension, and protoplast culture for several commercial lettuce cultivars Red Romaine Annapolis, Red Lollo Natividad, Red Grand Rapids Firecracker, Dark Red Lollo Rossa, Antago, Red Grand Rapids Blackhawk and Red Romaine Rhazes.

This is also the first description of tissue culture technology and mutagenesis methods for the development of lettuce cultivars with increased content of total polyphenols and anthocyanins and enhanced antioxidant capacity. A selection system based on anthocyanin color has been successfully utilized, and the darkest red/purple variants have been selected in tissue culture conditions. The lettuce plants produced yielded extremely high levels of polyphenols, anthocyanins and antioxidant capacity. Although several publications present data on anthocyanin content in different red lettuce cultivars growing under various growth conditions, including variable light intensity and temperature (11-14), the plants described herein have the highest content of anthocyanins, and in the best plants, this content is higher than in blueberry.

The present disclosure provides several new lettuce varieties that have increased amounts of the phytonutrients, anthocyanins and other polyphenols, as well as increased oxygen radical absorption capacity (ORAC). Examples include S-13, NFR-S-1, NFR-S-4, NFR-S-6, NBR-S-9, NBR-S-16, and NRR-S-21-1. These new varieties have about 1-3 times more anthocyanins, about 2-4 times more phenolics, and about 2-3 times more ORAC than other known varieties of lettuce. In one example, the new lettuce varieties have about 5 to 11 mg/g FW phenolics (measured in gallic acid equivalents) (such as at least 5, at least 6, at least 7, at least 8, at least 9, at least 10, or at least 11 mg/g FW phenolics), 0.5 to 3 mg/g FW anthocyanins (measured in cyanidin-3-glucoside equivalents) (such as at least 0.5, at least 1, at least 1.5, at least 2, at least 2.5, or at least 3 mg/g FW anthocyanins), and 100 to 300 µmol/g FW oxygen radical absorption capacity (measured in trolox equivalents) (such as at least 100, at least 150, at least 200, at least 225, at least 250, at least 275, or at least 300 µmol/g FW oxygen radical absorption capacity). Methods of measuring total phenolic content are known, and the disclosure is not limited to particular methods. In one example, a Folin-Ciocalteu phenol reagent is used. Methods of measuring total monomeric anthocyanin and proanthocyanidin content are known, and the disclosure is not limited to particular methods. In one example, an AOAC pH differential method or a 4-dimethylaminocinnamaldehyde method is used. Methods of measuring ORAC are known, and the disclosure is not limited to particular methods. In one example, Trolox® is used.

In some examples, the new lettuce varieties have at least 10 mg/g DW chlorogenic acid (such as at least 12, at least 15, at least 20, at least 21, at least 22, at least 23, at least 24, at least 25, at least 26, or at least 27 mg/g chlorogenic acid), at least 4 mg/g DW quercetin 3 glucoside (such as at least at least 5, at least 6, at least 7, at least 8, at least 8.5, at least 9, at least 10, at least 11, at least 12, or at least 13 mg/g DW quercetin 3 glucoside), at least 10 mg/g DW quercetin malonylglucoside (such as at least at least 12, at least 15, at least 8, at least 20, at least 25, at least 26, at least 27, at least 28, at least 29, at least 30, or at least 31 mg/g DW quercetin malonylglucoside), at least 7 mg/g cyanidin malonylglucoside (such as at least at least 8, at least 10, at least 12, at least 15, at least 15.5, at least 16, at least 17, at least 18, at least 19, or at least 20 mg/g cyanidin malonylglucoside), or combinations thereof.

Thus provided herein are seeds of the new lettuce varieties, wherein representative sample seed of the varieties are deposited under (ATCC Accession Nos. PTA-120680, PTA-120681 and PTA-120682). Also provided are lettuce seed mixtures containing such seeds, such as mixtures of the disclosed varieties, as well as mixtures containing other known lettuces. The disclosure provides lettuce plants having or consisting of the morphological and physiological characteristics of one or more of the new lettuce varieties provided herein. The disclosure also provides lettuce plants having one or more of the morphological and physiological characteristics of the new lettuce varieties (such as those listed in Table 3). In one example, such plants have or include the characteristics noted in Table 3, for example increased amounts of the phytonutrients, anthocyanins and polyphenols. Also provided are seeds of such plants, progeny of such plants, parts of such plants (such as pollen, ovules and cells), and vegetative sprigs or clones of such plants. In one example, the disclosure provides lettuce plants having the genotype of one or more of the new lettuce varieties provided herein. For example, the disclosure provides plants produced by growing the seed of the new lettuce varieties provided herein.

The disclosed new lettuce plants, and in some examples progeny thereof, have increased amounts of anthocyanins and polyphenols as compared to other lettuces. For example, the disclosed new lettuces, and in some examples progeny thereof, have at least 5 mg/g FW phenolics (measured in gallic acid equivalents), such as at least 6 mg/g FW phenolics, at least 7 mg/g FW phenolics, at least 8 mg/g FW phenolics, at least 9 mg/g phenolics, at least 10 mg/g FW phenolics, or at least 11 mg/g FW phenolics (measured in gallic acid equivalents). In some examples, the disclosed new lettuce varieties, and in some examples progeny thereof, have an amount of phenolics that is at least 2-fold, at least 2.5 fold, at least 2.7 fold, at least 3-fold, at least 3.5-fold, or at least 4-fold greater than other lettuces (such as Red Romaine Annapolis, Red Grand Rapids Firecracker, Red Grand Rapids Blackhawk, Dark Red Lollo Rossa, Romaine, and Boston). For example, the disclosed new lettuces, and in some examples progeny thereof, have at least 0.5 mg/g FW anthocyanins (measured in cyanidin-3-glucoside equivalents), such as at least 1 mg/g FW anthocyanins, at least 1.2 mg/g FW anthocyanins, at least 1.5 mg/g FW anthocyanins, at least 2 mg/g FW anthocyanins, at least 2.2 mg/g FW anthocyanins, or at least 2.4 mg/g FW anthocyanins (measured in cyanidin-3-glucoside equivalents). In some examples, the disclosed new lettuce varieties, and in some examples progeny thereof, have an amount of anthocyanins that is at least 1-fold, at least 1.5 fold, at least 2 fold, at least 2.5-fold, at least 3-fold, or at least 3.5-fold greater than other lettuces (such as Red Romaine Annapolis, Red Grand Rapids Firecracker, Red Grand Rapids Blackhawk, Dark Red Lollo Rossa, Romaine, and Boston).

The disclosed new lettuce varieties and seeds can be used to produce other lettuce plants and seeds, for example as part of a breeding program. Choice of breeding or selection methods using to generate new lettuce plants and seeds can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location can be effective, whereas for traits with low heritability, selection can be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used extensively for breeding disease-resistant varieties (e.g., see Bowers et al., 1992. *Crop Sci.* 32(1):67-72; Nickell and Bernard, 1992. *Crop Sci.* 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

A difficult task is the identification of individuals that are genetically superior, because for most traits the true genotypic value can be masked by other confounding plant traits or environmental factors. One method of identifying a superior plant is to observe its performance relative to other experimental plants and to one or more widely grown standard varieties. Single observations can be generally inconclusive, while replicated observations provide a better estimate of genetic worth.

Plant breeding can result in new, unique and superior lettuce varieties and hybrids from the disclosed new lettuce varieties. Two or more parental lines can be selected (such as one of the disclosed new lettuce varieties as one of the lines), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season. The varieties developed can be unpredictable, because the selection occurs in unique environments, with no control at the DNA level (using conventional breeding procedures), and with millions of different possible genetic combinations being generated.

The development of new lettuce varieties from the disclosed varieties involves the development and selection of lettuce varieties, the crossing of these varieties and selection of progeny from the superior hybrid crosses. A hybrid seed is produced by manual crosses between selected male-fertile parents or by using male sterility systems. Hybrids can be identified by using certain single locus traits such as flower color, pubescence color or herbicide resistance which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is one of the new varieties provided herein) which possess favorable, complementary traits are crossed to produce an $F_1$. An F2 population is produced by selfing one or several $F_1$'s. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (e.g., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent (e.g., one of the new varieties disclosed herein). The source of the trait to be transferred is called the donor or nonrecurrent parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, one or more seeds from each plant in a population are commonly harvested and threshed together to form a bulk. Part of the bulk is used to plant the next generation and part is put in reserve. The multiple-seed procedure makes it possible to plant the same number of seeds of a population each generation of inbreeding. Sufficient numbers of seeds are harvested to make up for those plants that did not germinate or produce seed.

Descriptions of other breeding methods that are commonly used for different traits and crops can be found in one of several reference books (e.g., Allard. 1960. Principles of plant breeding. Davis, Calif.: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987).

Breeding New Lettuce Varieties with Increased Anthocyanins and Polyphenols

Methods for crossing the new lettuce varieties provided herein (such as S-13, NBR-S-16, NRR-S-21 and NFR-S-4) with itself or a second plant are provided, as are the seeds and plants produced by such methods. Such methods can be used for propagation of one or more of the new lettuce varieties provided herein, or can be used to produce hybrid lettuce seeds and the plants grown therefrom. Hybrid lettuce plants can be used, for example, in the commercial production of lettuce products (including extracts) or in breeding programs for the production of novel lettuce varieties. A hybrid plant can also be used as a recurrent parent at any given stage in a backcrossing protocol during the production of a single locus conversion (for example introduction of one or more desirable traits) of the new lettuce varieties provided herein.

Methods of producing lettuce plants and/or seed are provided. Such a method can include crossing a new lettuce variety provided herein with itself or a second lettuce plant and harvesting a resulting lettuce seed, such as an $F_1$ hybrid seed. The resulting plant can be grown, resulting in a lettuce plant or part thereof.

In one example methods of producing an inbred lettuce plant derived from a new lettuce variety provided herein are provided. In one example such methods include (a) preparing a progeny plant derived from a new lettuce variety provided herein by crossing a plant of the new variety with a lettuce plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred lettuce plant derived from a new lettuce variety provided herein.

The second plant crossed with a new lettuce variety provided herein for the purpose of developing novel lettuce varieties, is typically a plant which either themselves exhibit one or more desirable characteristics or which exhibit one or more desired characteristic(s) when in hybrid combination. In one example, the second lettuce plant is transgenic. Exemplary desired characteristics include, but are not limited to: increased seed yield, increased seedling vigor, modified maturity date, desired plant height, high anthocyanin content, high phenolic content, herbicide tolerance or resistance, drought tolerance or resistance, heat tolerance or resistance, low or high soil pH level tolerance, salt tolerance or resistance, resistance to an insect, resistance to a bacterial disease, resistance to a viral disease, resistance to a fungal disease, resistance to a nematode, resistance to a pest, male sterility, site-specific recombination, abiotic stress tolerance, and modified antioxidant characteristics.

When a new lettuce variety provided herein is crossed with another different variety, first generation ($F_1$) lettuce progeny are produced. The hybrid progeny are produced regardless of characteristics of the two varieties produced. As such, an $F_1$ hybrid lettuce plant can be produced by crossing a new lettuce variety provided herein with any second lettuce plant. The second lettuce plant can be genetically homogeneous (e.g., inbred) or can itself be a hybrid. Therefore the disclosure provides any $F_1$ hybrid lettuce plant produced by crossing a new lettuce variety provided herein with a second lettuce plant (such as a transgenic plant having one or more genes that confer to the plant one or more desired characteristics).

Lettuce plants can be crossed by either natural or mechanical techniques. Natural pollination occurs in lettuce either by self-pollination or natural cross pollination, which typically is aided by pollinating organisms. In either natural or artificial crosses, flowering and flowering time can be a consideration.

Sensitivity to day length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting. Lettuces can be grown in winter nurseries located at sea level in tropical latitudes where day lengths are shorter than their critical photoperiod. The short day lengths and warm temperatures encourage early flowering and seed maturation. Early flowering can be useful for generation advance when only a few self-pollinated seeds per plant are desired, but usually not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of plants. It can influence the time of flowering and suitability of flowers for hybridization. Artificial hybridization is typically successful between about 26° C. and about 32° C.

Self-pollination can occur naturally in lettuce with no manipulation of the flowers. In some examples, the crossing of two lettuce plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated using known methods. Exemplary methods for emasculating the male parts of a lettuce flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization. Grafting can be used to hasten the flowering of late flowering genotypes.

Lettuce Plants Having One or More Desired Heritable Traits

The disclosure provides plants of the new lettuce varieties modified to include one or more desired heritable traits. In some examples, such plants can be developed using backcrossing or genetic engineering (for example by introducing one or more transgenes into the disclosed new lettuce varieties, such as S-13, NBR-S-16, NRR-S-21 and NFR-S-4, wherein the transgenes encode one or more desired traits), wherein essentially all of the desired morphological and physiological characteristics of the new lettuce variety are recovered (such as increased anthocyanins and/or phenolics) in addition to a genetic locus transferred into the plant via the backcrossing technique. Plants developed using such methods can be referred to as a single locus converted plant.

In one example, the method of introducing one or more desired traits into one or more of the disclosed new lettuce varieties includes (a) crossing a plant of one of the new varieties with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of the new variety to produce backcross progeny plants; (d) selecting backcross progeny plants that have the one or more desired traits and physiological and morphological characteristics of the new lettuce variety to produce selected backcross progeny plants; and (e) repeating steps (c) and (d) one or more times in succession to produce selected second or higher backcross progeny plants that have the one or more desired traits and the physiological and morphological characteristics of the original new lettuce variety when grown in the same environmental conditions.

Backcrossing methods can be used to improve or introduce a characteristic into the new lettuce varieties. The parental lettuce plant which contributes the locus for the desired characteristic is termed the "nonrecurrent" or "donor" parent. This terminology refers to the fact that the nonrecurrent parent is used one time in the backcross protocol and therefore does not recur. The parental lettuce plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Sprague and Dudley, eds. 1988. Corn and Improvement, 3rd edition). In a typical backcross protocol, the original variety of interest (recurrent parent, e.g., one of the new lettuce varieties disclosed herein) is crossed to a second variety (nonrecurrent parent) that carries the single locus of interest (such as a desirable trait) to be transferred. The resulting progeny from this cross are then crossed again to the recurrent parent and the process is repeated until a lettuce plant is obtained wherein essentially all of the desired morphological and physiological characteristics of the recurrent parent (e.g., one of the new lettuce varieties disclosed herein) are recovered (such as increased anthocyanins and/or phenolics) in the converted plant, in addition to the single transferred locus from the nonrecurrent parent.

The goal of a backcross protocol is to alter or substitute a single trait or characteristic in the original variety, such as one of the new lettuce varieties disclosed herein. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent can be composited without the usual replicated tests for traits such as yield, in the individual lines.

Lettuce varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus characteristics, modified antioxidant characteristics, yield stability, and yield enhancement. These comprise genes generally inherited through the nucleus. Thus plants of one of the new lettuce varieties disclosed herein that include a single locus conversion (such as one that confers a desired trait) are provided herein.

Direct selection can be applied where the single locus acts as a dominant trait. An example of a dominant trait is the herbicide resistance trait (such as glyphosate resistance). For the selection process, the progeny of the initial cross are sprayed with a herbicide (such as RoundUp® herbicide) prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of lettuce plants for breeding may not be dependent on the phenotype of a plant and instead can be based on genetic investigations. For example, a suitable genetic marker can be used which is closely genetically linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to the breeding of lettuce are well known in the art. Such methods can be useful in the case of recessive traits and variable phenotypes, or where conventional assays are more expensive, time consuming or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Qualitative characters can be useful as phenotype-based genetic markers in lettuce; however, some or many may not differ among varieties commonly used as parents. Exemplary genetic markers include flower color, differences in maturity, height, and pest resistance.

Useful or desirable traits can be introduced by backcrossing, as well as directly into a plant by genetic transformation methods. Genetic transformation can therefore be used to insert a selected transgene into one of the new lettuce varieties disclosed herein or can, alternatively, be used for the preparation of transgenes which can be introduced by backcrossing. Thus, the disclosure provides methods of producing a plant of one of the new lettuce varieties disclosed herein that includes one or more added desired traits, for example that include introducing a transgene(s) conferring the one or more desired traits into one of the new lettuce varieties disclosed herein (for example by transformation with a transgene that confers upon the lettuce plant the desired trait), thereby producing a plant of one of the new lettuce varieties disclosed herein that includes the one or more added desired traits.

Methods for the transformation of many economically important plants, including lettuces, are well known. Methods for introducing a desired nucleic acid molecule (e.g., transgene), such as DNA, RNA, or inhibitory RNAs, are well known in the art, and the disclosure is not limited to particular methods. Exemplary techniques which can be employed for the genetic transformation of lettuce include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner. Protoplasts can also be employed for electroporation transformation of plants (Bates. 1994. *Mol. Biotechnol.* 2(2):135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

*Agrobacterium*-mediated transfer is a well-known method in the art for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed—genes can be used for transformation. The use of *Agrobacterium*-mediated plant integrating vectors to introduce DNA into plant cells is well known (e.g., Fraley et al. 1985. *Bio. Tech.* 3(7):629-635; U.S. Pat. No. 5,563,055). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457).

In one example, such methods can also be used to introduce transgenes for the production of proteins in transgenic lettuces. The resulting produced protein can be harvested from the transgenic lettuce. The transgene can be harvested from the transgenic plants that are originated or are descended from one of the new lettuce varieties disclosed herein, a seed of such a lettuce or a hybrid progeny of such a lettuce.

Numerous different genes are known and can be introduced into one of the new lettuce varieties disclosed herein or progeny thereof. Non-limiting examples of particular genes and corresponding phenotypes that can be chosen for introduction into a lettuce plant are provided herein.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to a herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Mild et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Genes conferring resistance to a herbicide that inhibits photosynthesis are also known, such as, a triazine (psbA and gs+ genes) and a benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseudomonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Disease Resistance

Plant defenses are often activated by specific interaction between the product of a disease resistance gene (R) in the plant and the product of a corresponding avirulence (Avr) gene in the pathogen. A plant, such as one of the new lettuce varieties disclosed herein or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium fulvum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease.

Insect Resistance

One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Δendotoxin gene). Moreover, DNA molecules encoding Δ-endotoxin genes can be purchased from the ATCC (Manassas, Va.), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WIPO Publication No. WO 1994/000992, which teaches the use of avidin and avidin homologues as larvicides against insect pests.

In one example the insect resistance gene is an enzyme inhibitor, for example, a protease, proteinase inhibitor, or an α-amylase inhibitor. See, for example, Abe et al. (1987.1 *Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

Male Sterility

Genetic male sterility can increase the efficiency with which hybrids are made, in that it can eliminate the need to physically emasculate the lettuce plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the lettuce plant is utilized. However, in many cases, the seeds are considered to be a valuable portion of the crop, thus, it is desirable to restore the fertility of the hybrids in these crops. Therefore, the disclosure provides plants of one of the new lettuce varieties disclosed herein comprising a genetic locus capable of restoring male fertility in an otherwise male-sterile plant. Examples of male-sterility genes and corresponding restorers which can be employed are well known (see, e.g., U.S. Pat. No. 5,530,191 and U.S. Pat. No. 5,684,242).

Tissue Cultures and In Vitro Regeneration of Lettuce Plants

Tissue cultures of the new lettuce varieties are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, petiole, stein, ovule, cotyledon, hypocotyl, shoot or stem, and the like. In a particular example, the tissue culture includes embryos, protoplasts, meristematic cells, pollen, leaves or anthers of one of the new lettuce varieties disclosed herein. Also provided are lettuce plants regenerated from such tissue cultures, wherein the regenerated lettuce plant expresses the physiological and morphological characteristics of at least one of the new lettuce varieties disclosed herein.

Methods for preparing tissue cultures of regenerable lettuce cells and regenerating lettuce plants therefrom, are known, such as those disclosed in U.S. Pat. Nos. 4,992,375; 5,015,580; 5,024,944, and 5,416,011. Tissue culture provides the capability to regenerate fertile plants. This can allow, for example, transformation of the tissue culture cells followed by regeneration of transgenic plants. For transformation to be efficient and successful, DNA can be introduced into cells that give rise to plants or germ-line tissue.

Lettuces can be regenerated using shoot morphogenesis or somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos, while lines that produce large numbers of embryos during an "induction" step may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Shoot morphogenesis is a system whereby shoots are obtained de novo from cotyledonary nodes of lettuce seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis in lettuce is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer" embryos.

Embryogenic cultures can also be used for regeneration, including regeneration of transgenic plants.

Improved Regeneration Methods and Medium

The inventors have identified improved regeneration methods. In particular examples, the method includes culturing lettuce cotyledons (e.g., from plants not more than 10 days old, such as 3-7 days old, such as 5 days old) or young leaves (e.g., from plants not more than 3 weeks old, such as 1-3 weeks old, such as 2 weeks old) in the presence of 6-benzylaminopurine (BAP), zeatin and naphthaleneacetic acid (NAA), such as at least 0.1 mg/l BAP (such as at least 0.5 mg/l, at least 0.75 mg/l, at least 1 mg/l, or at least 2 mg/l BAP, such as 0.1 to 5 mg/l BAP, 0.1 to 3 mg/l BAP, 0.5 to 2 mg/l BAP, or 0.5 to 1.5 mg/l BAP, such as 1 mg/l BAP); at least 0.05 mg/l zeatin (such as at least 0.1 mg/l, at least 0.5 mg/l, at least 0.75 mg/l, or at least 1 mg/l zeatin, such as 0.1 to 5 mg/l zeatin, 0.2 to 3 mg/l zeatin, 0.2 to 1 mg/l zeatin, or 0.3 to 1 mg/l zeatin, such as 0.5 mg/l zeatin); and at least 0.02 mg/l NAA (such as at least 0.05 mg/l, at least 0.075 mg/l, at least 0.1 mg/l, at least 0.2 mg/l, at least 0.5 mg/l NAA, or at least 2 mg/l NAA, such as 0.05 to 2 mg/l NAA, 0.1 to 2 mg/l NAA, 0.1 to 1 mg/l NAA, or 0.1 to 0.5 mg/l NAA, such as 0.2 mg/l NAA). In a specific example, the cotyledons or young leaves can be cultured in the presence of 0.1 to 5 mg/l BAP; 0.1 to 5 mg/l zeatin; and 0.05 to 2 mg/l NAA. For example, the cotyledons or young leaves can be cultured in medium, such as MS medium containing these hormones in a petri dish. It is shown herein that this method was efficient for six lettuce varieties belonging to loose leaf and Romaine types.

Also provided herein are regeneration medium that can be used to culture cotyledons and leaves, such as a medium that includes BAP, zeatin and NAA, such as at least 0.1 mg/l BAP (such as at least 0.5 mg/l, at least 0.75 mg/l, at least 1 mg/l, or at least 2 mg/l BAP, such as 0.1 to 5 mg/l BAP, 0.1 to 3 mg/l BAP, 0.5 to 2 mg/l BAP, or 0.5 to 1.5 mg/l BAP, such as 1 mg/l BAP); at least 0.05 mg/l zeatin (such as at least 0.1 mg/l, at least 0.5 mg/l, at least 0.75 mg/l, or at least 1 mg/l zeatin, such as 0.1 to 5 mg/l zeatin, 0.2 to 3 mg/l zeatin, 0.2 to 1 mg/l zeatin, or 0.3 to 1 mg/l zeatin, such as 0.5 mg/l zeatin); and at least 0.02 mg/l NAA (such as at least 0.05 mg/l, at least 0.075 mg/l, at least 0.1 mg/l, at least 0.2 mg/l, at least 0.5 mg/l NAA, or at least 2 mg/l NAA, such as 0.05 to 2 mg/l NAA, 0.1 to 2 mg/l NAA, 0.1 to 1 mg/l NAA, or 0.1 to 0.5 mg/l NAA, such as 0.2 mg/l NAA). In one example, the regeneration medium include MS medium containing these hormones.

Improved Methods of Making New Lettuce Varieties with Increased Anthocyanins

The inventors have identified improved methods of generating new lettuce varieties that have increased anthocyanins. This is the first report of propagation in vitro conditions, callus induction, cell suspensions, protoplast cultures and development of regeneration systems for commercial lettuce varieties Red Romaine Annapolis, Red Grand Rapids Firecracker, Red Grand Rapids Blackhawk, Dark Red Lollo Rossa, Red Lollo Natividad, Red Lollo Antago and Red Romaine Rhazes. This is also the first report on the use of tissue culture technology and mutagenesis for development of lettuce varieties with high anthocyanin and polyphenol content and increased oxygen radical absorption capacity.

In particular examples, the method includes culturing lettuce parts, such as cotyledons (e.g., from plants not more than 10 days old, such as 3-7 days old, such as 5 days old) or young leaves (e.g., from plants not more than 3 weeks old, such as 1-3 weeks old, such as 2 weeks old) in the hormones and medium as described above. In other examples, the method includes incubating callus cultures or cell suspension in R9 medium (see Table 1) that contains cytokinins, such as BAP and zeatin, for example at least 0.1 mg/l BAP, and at least 0.1 mg zeatin, such as at least 0.5 mg/l, at least 1 mg/l, or at least 2 mg/l BAP and zeatin, such as 1 mg/l BAP and 1 mg/l zeatin. In other examples, the method includes incubating protoplasts in MS medium (see Table 1) that contains hormones such as BAP and NAA, for example at least 0.1 mg/l BAP and at least 0.01 mg NAA, such as at least 0.5 mg/l, at least 1 mg/l, or at least 2 mg/l BAP and at least 0.05 mg/l, at least 0.75 mg/l, at least 0.1 mg/l, at least 0.5 mg/l or at least 1 mg/l NAA, such as 1 mg/l BAP and 0.1 mg/l NAA.

The lettuce parts, such as cotyledons, young leaves, calli or protoplasts, are regenerated until shoots are produced. In some examples, lettuce parts, such as cotyledons, young leaves, protoplasts, or calli are illuminated with blue light (e.g., 10 to 45 nm) during growth to improve selection of red tissues of lettuce cultivars. The most red/purple shoots/segments are selected and can be cut into pieces and placed again on the regeneration medium. Multiple rounds of screening can be performed, such as at least 2, at least 3, at least 5 or at least 10 rounds of screening for dark red/purple color. Thus, accumulation of anthocyanins can be used as visual selection marker. The resulting final selected lines can be transferred for root induction and later to the greenhouse.

Lettuce seeds can be mutagenized by treatment with ethyl methanesulfonate (EMS) and/or N-Nitroso-N-methylurea (NMU). The resulting cotyledons can be grown on regeneration medium as described above, and the darkest red/purple shoots selected. Several rounds of regeneration can be performed. In another example, the resulting red/purple shoots selected can then be further mutagenized using UV-A light (for example for at least 1 minute, at least 2 minutes, at least 5 minutes, or at least 10 minutes, such as 5 to 15 minutes). In some example, the shoots are treated with UV-A light more than once, such as at least 2, at least 3, at least 4, at least 5, at least 6, at least 7, at least 8, at least 9, or at least 10 times, such as 5 to 15 times.

Methods of Making Extracts from Lettuce

The new varieties disclosed herein (such as S-13, NBR-S-16, NRR-S-21 and NFR-S-4) can be used to generate anthocyanin-containing extracts. Methods of generating extracts are routine, and the disclosure is not limited to particular methods of making the extract.

In one example, lettuce leaves or any above-ground part from one or more the varieties disclosed herein are harvested, for example, after at least 20 days, at least 30 days, at least 45 days, at least 60 days, at least 70 days, or at least 90 days of growth (such as after 30 to 90 days, 45 to 80 days, or 60 to 75 days, such as after 70 days of growth). In some examples, the leaves are used directly. In some examples, the leaves are frozen and then dried (for example by air drying, microwaving, lyophilization, or combinations thereof).

The leaves or dried material can be ground, for example to a fine powder. The resulting powder can be used directly (for example for use in a tablet or capsule), or can be dissolved or suspended in a carrier, such as a pharmaceutically acceptable carrier such as saline (for example suitable for injection). In some example, the resulting powder is placed in an extraction solvent and the resulting supernatant used. For example, the powder can be extracted with acidified water (hot or at room temperature), or 20-80% ethanol, which can also be acidified (for example with acetic, hydrochloric or sulfuric acids).

In one example, the lettuce extract is formulated into a pharmaceutical composition, for example alone or with a pharmaceutically acceptable carrier. The pharmaceutically acceptable carriers useful herein are conventional. *Remington's Pharmaceutical Sciences*, by Martin, Mack Publishing Co., Easton, Pa., 15th Edition (1975), describes compositions and formulations suitable for pharmaceutical delivery of the lettuce extracts herein disclosed. In general, the nature of the carrier will depend on the mode of administration of the lettuce extract being employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition containing the lettuce extract can be a liquid solution, suspension, emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

Methods of Stabilizing Blood Glucose Levels

The disclosed new lettuces (such as S-13, NBR-S-16, NRR-S-21 and NFR-S-4) and extracts thereof can be used to reduce blood glucose levels, for example in a subject in need thereof, such as a mammal having or diabetes (such as type 2 diabetes) or pre-diabetes. Thus, in some examples the disclosed new lettuces and extracts thereof can be used to treat diabetes (such as type 2 diabetes), for example alone or in combination with insulin.

Exemplary subjects that can be treated with or be administered the disclosed new lettuces and extracts thereof include but are not limited to, humans and veterinary subjects, such as cats and dogs. In some examples, the subject treated is obese (e.g., having a body mass index of more than 30 kg/m$^2$, such as 30 kg/m$^2$-50 kg/m$^2$). In some examples, the subject treated has a fasting glucose of at least 126 mg/dl, such as at least 130 mg/dl).

In some examples, administration of the new lettuces or extracts thereof reduces fasting blood glucose in a subject by at least 10%, at least 15%, at least 20%, at least 21%, at least 22%, at least 23%, at least 24%, at least 25%, at least 26%, at least 27%, at least 28%, at least 29%, at least 30%, at least 31%, at least 35%, or at least 40% (such as 15 to 50%, 15 to 40% or 20 to 40%) (for example as compared to a vehicle control), for example as compared to the fasting blood glucose level prior to administering the new lettuces disclosed herein or extracts thereof. In one example, administration of the new lettuces or extracts thereof reduce fasting blood glucose in a subject by at least 10%, at least 15%, at least 20%, at least 21%, at least 22%, at least 23%, at least 24%, at least 25%, at least 26%, at least 27%, at least 28%, at least 29%, at least 30%, at least 31%, at least 35%, or at least 40% (such as 15 to 50%, 15 to 40% or 20 to 40%) (for example as compared to a vehicle control), for example with a fast of at least 1 hour, at least 2 hours, at least 3 hours, at least 4 hours, at least 5 hours, at least 6 hours, at least 8 hours or at least 12 hours prior to the administration, and wherein the administration reduces the FBG level by such amounts within 10 minutes, 30 minutes, 1 hour, 2 hours, 3 hours, 4 hours, 5 hours, 6 hours, 8 hours, or 12 hours following administering the new lettuces disclosed herein or extracts thereof. In one example, administration of the new lettuces or extracts thereof increase glucose metabolism in a subject measured by oral glucose tolerance tests by at least 10%, at least 15%, at least 20%, at least 21%, at least 22%, at least 23%, at least 24%, at least 25%, at least 26%, at least 27%, at least 28%, at least 29%, at least 30%, at least 31%, at least 35%, or at least 40% (such as 15 to 50%, 15 to 40% or 20 to 40%) (for example as compared to a vehicle control), for example as measured following a fast of at least 1 hour, at least 2 hours, at least 3 hours, at least 4 hours, at least 5 hours, at least 6 hours, at least 8 hours or at least 12 hours, and with an oral glucose challenge within 10 minutes, 30 minutes, 60 minutes, 90 minutes, 2 hours, 3 hours, 4 hours, 5 hours, 6 hours, 8 hours, or 12 hours of measuring the blood glucose levels.

Methods of administering the new lettuces and extracts thereof include, but are not limited to, topical, intradermal, intramuscular, intraperitoneal, intravenous, subcutaneous, intranasal, and oral routes. The compounds can be administered by any convenient route, for example by infusion or bolus injection, by absorption through epithelial or mucocutaneous linings (for example, oral mucosa, rectal, vaginal and intestinal mucosa, etc.) and can be administered together with other biologically active agents (such as insulin or metformin). In a particular example, the new lettuces or extracts thereof are administered by feeding the lettuce or extract to the subject.

In some examples, the amount of lettuce or extract thereof administered is at least 1 mg/kg body weight of the subject, at least 5 mg/kg body weight of the subject, at least 10 mg/kg body weight of the subject, at least 25 mg/kg body weight of the subject, at least 50 mg/kg body weight of the subject, at least 100 mg/kg body weight of the subject, at least 200 mg/kg body weight of the subject, at least 300 mg/kg body weight of the subject, at least 400 mg/kg body weight of the subject, at least 450 mg/kg body weight of the subject, at least 400 mg/kg body weight of the subject, for example 1 to 1000, 10 to 500, 100 to 500, 100 to 450, 300 to 500, 50 to 100 or 75 to 100 mg/kg body weight of the subject.

EXAMPLE 1

Methods of Making New Lettuce Cultivars with Increased Anthocyanins

Propagation In Vitro Conditions

Seeds of several lettuce cultivars (Red Romaine Rhazes, Red Romaine Annapolis, Red Lollo Natividad, Red Grand Rapids Firecracker, Dark Red Lolla Rossa, Red Lollo Antago and Red Grand Rapids Blackhawk; FIG. 1) were surface sterilized by immersion in 70% ethanol for 1 min, followed by a 1.2% sodium hypochlorite solution for 15 min. Seeds were rinsed 3 times with sterilized distilled water, and 20-25 seeds were placed in each Magenta GA-7 container, with 40 ml of germination medium (modified MS medium (18), Table 1). Medium pH was adjusted to 5.7, followed by agar addition, and autoclaving at 121° C., 103 kPa for 20 min. Seeds were germinated at 23° C. with a 16 h-light/8 h-dark photoperiod.

TABLE 1

Media used for tissue culture experiments.

| Name | Media composition |
|---|---|
| MS | Basic MS basal medium* with 3% sucrose, 0.7 % agar |
| MSG | ½ MS with 1% sucrose, 0.7 % agar |
| MSP | MS with 0.5 mg/l BAP, 3% sucrose, 0.7 % agar |
| MSC3 | MS with 0.3 mg/l BAP, 2 mg/l NAA, 0.2 mg/l 2,4-D, 3% sucrose, 0.7% agar |
| MSC4 | MS with 1 mg/l 2,4-D 3% sucrose, 0.7% agar |
| MSCS | MS with 3% sucrose, 0.5 mg/l 2,4-D |
| R7 | MS with 1 mg/l BAP, 0.5 mg/l zeatin, 0.2 mg/l NAA 3% sucrose, 0.7% agar |
| R9 | MS with 1 mg/l BAP, 1 mg/l zeatin |

In vitro cultures were maintained by transferring 1-cm-long stem segments with axillary buds onto MS medium, with subculture every 5-6 weeks onto fresh medium. For production of large amounts of plant material, shoot cultures were developed. For initiation and propagation of shoot cultures, MS medium with BAP (0.2, 0.5, 1 mg/l) was used. For root induction, well developed shoots were excised and transferred to MS medium.

Plant Regeneration from Cotyledons and Leaves

Several lettuce cultivars were evaluated for their organogenesis potential using plant hormones 6-benzylaminopurine (BAP), zeatin, kinetin, naphthaleneacetic acid (NAA) and 2,4-dichlorophenoxyacetic acid (2,4-D) in various combinations. The cotyledon explants were aseptically excised from 5-day-old seedlings, cut in half, and placed on 25 ml of regeneration medium in Petri plates (100×15 mm). Leaf explants (0.7×0.7 mm) were excised from 2-week-old and 2-month-old aseptically grown plants and placed on regeneration medium in Petri plates. Eight explants were placed on Petri plates, cultivated for 6 weeks and tested for shoot regeneration efficiency. For each experiment, at least 100 explants of each cultivar were used.

Callus Induction, Plant Regeneration from Callus

Leaf segments (0.7×0.7 cm) were cut from 3-4 week-old in vitro propagating lettuce shoot cultures and placed in Petri plates (100×15 mm) on MS medium supplemented with various concentrations of plant growth regulators: NAA (1-2 mg/l), BAP (0.3-0.5 mg/l) and 2.4-D (0.2 mg/l) for callus induction. Plates were incubated without light at 23° C. for 4-6 weeks. Well-developed calli were selected and transferred to MS medium supplemented with 1 mg/l 2.4-D (MSC4, Table 1). Callus tissues were maintained on MSC4 medium at 3- to 4-week intervals. Cell suspensions were established from callus tissues on liquid MSCS medium. Maintenance of cell suspension was carried out on MSCS medium at 10-14 day-intervals.

Protoplasts Culture

Protoplasts were isolated from aseptically grown shoot cultures. The protoplast isolation and purification was performed according to the protocol of Gleba et al. (19). Protoplasts were cultured in medium MO2 (19) for 2 weeks, followed by colony transfer onto medium M (19) with reduced osmotic pressure. Shoot regeneration was induced on MS medium containing 1 mg/l BAP and 0.1 mg/l NAA (20). Shoots were rooted by transferring onto MS medium without hormones.

Chemical Mutagenesis of Seeds

Lettuce seeds were soaked in distilled water and treated as described (21), with freshly prepared 0.3% (wt/vol) ethyl methanesulfonate (EMS) or 5 mM N-Nitroso-N-methylurea (NMU) for 20-24 hours. They were maintained on a rotary shaker (100 rpm) at room temperature. Seeds were thoroughly washed in running tap water, surface sterilized with 70% ethanol and 1.2% sodium hypochlorite solution, rinsed with sterile distilled water and placed on MS medium for germination. Cotyledons from EMS- and NMU-treated seeds were cut into small pieces and placed on regeneration medium. After 6-8 weeks, the darkest red/purple shoots were selected, cut into pieces, and placed again on regeneration medium. After several rounds of regeneration, the darkest red/purple shoots were transferred for root induction. Plants with roots were transferred to greenhouse.

UV-A Treatment of Leaves, and Callus Tissues.

Shoot cultures growing in vitro conditions were treated by UV-A for 10 min. After treatment, cultures were cultivated in the dark for 24 h, then transferred to light. Treatment was repeated 8 times. Young leaves were cut into pieces and placed onto regeneration medium for selection of red shoots. Callus tissues were treated by UV-A for 20 min, and the treatment repeated 8 times. After 3-4 weeks, callus tissues were transferred to regeneration medium R9 (Table 1).

Growth in Greenhouse

Lettuce cultivars Red Lollo Natividad, Red Grand Rapids Firecracker, Dark Red Lollo Rossa, Red Lollo Antago, Red Grand Rapids Blackhawk, Red Romaine Annapolis, and Red Romaine Rhazes were grown hydroponically in greenhouse conditions under a 16-h light/8-h dark photoperiod at 23° C.-20° C. Leaves were sampled from nine-week-old plants.

EXAMPLE 2

Development of Tissue Culture Methods

In Vitro Propagation.

For establishment of in vitro cultures seeds of five leaf-type lettuce (cvs. Red Lollo Natividad, Red Grand Rapids Firecracker, Dark Red Lollo Rossa, Red Lollo Antago, Red Grand Rapids Blackhawk) and two Romaine-type lettuce (Red Romaine Annapolis and Red Romaine Rhazes) were surface sterilized. After 2-4 days seeds were germinated on the MSG medium. Aseptic plantlets were produced for all seven cultivars. Shoot cultures were initiated from all cultivars to provide a convenient and uniform source of starting material. The highest number of shoots was obtained on MS medium supplemented with 0.5 mg/l BAP (MSP medium, Table 1).

Development of Regeneration System.

An important step in tissue culture manipulations is to develop efficient regeneration protocol. Testing of different type of explants (cotyledons, young and old leaves) showed that cotyledons had the best regeneration potential. Different combinations of cytokinins and auxins in MS medium were evaluated for shoot regeneration (Table 2).

TABLE 2

Table 2. Medium used for plant regeneration

| Hormones, mg/l | Regeneration MS Media | | | | | | | | | | |
|---|---|---|---|---|---|---|---|---|---|---|---|
| | R1 | R2 | R3 | R4 | R5 | R6 | R7 | R8 | R9 | R10 | R11 |
| BAP | 1 | — | — | 2 | 1 | 1 | 1 | 0.5 | 1 | 1 | 2 |
| Zeatin | — | 1 | — | — | 1 | 0.5 | 0.5 | — | 1 | 0.5 | — |
| Kinetin | — | — | 1 | — | — | — | — | — | — | — | — |
| NAA | 0.1 | 0.1 | 0.1 | 0.1 | 0.1 | 0.1 | 0.2 | — | — | 0.1 | 0.1 |
| 2,4-D | — | — | — | — | — | — | — | — | — | 0.1 | 0.2 |

Figures 2A, 2B:
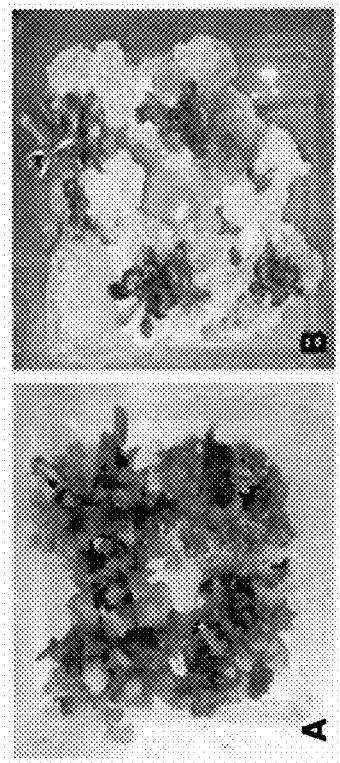
FIGS. 2A and 2B are digital images showing an assessment of regeneration procedures for lettuce. (A) Regeneration response from cotyledon explants (cv. Red Grand Rapids Firecracker) and (B) shoot formation from callus tissues (cv. Red Romaine Annapolis, remove).
Figure 3:
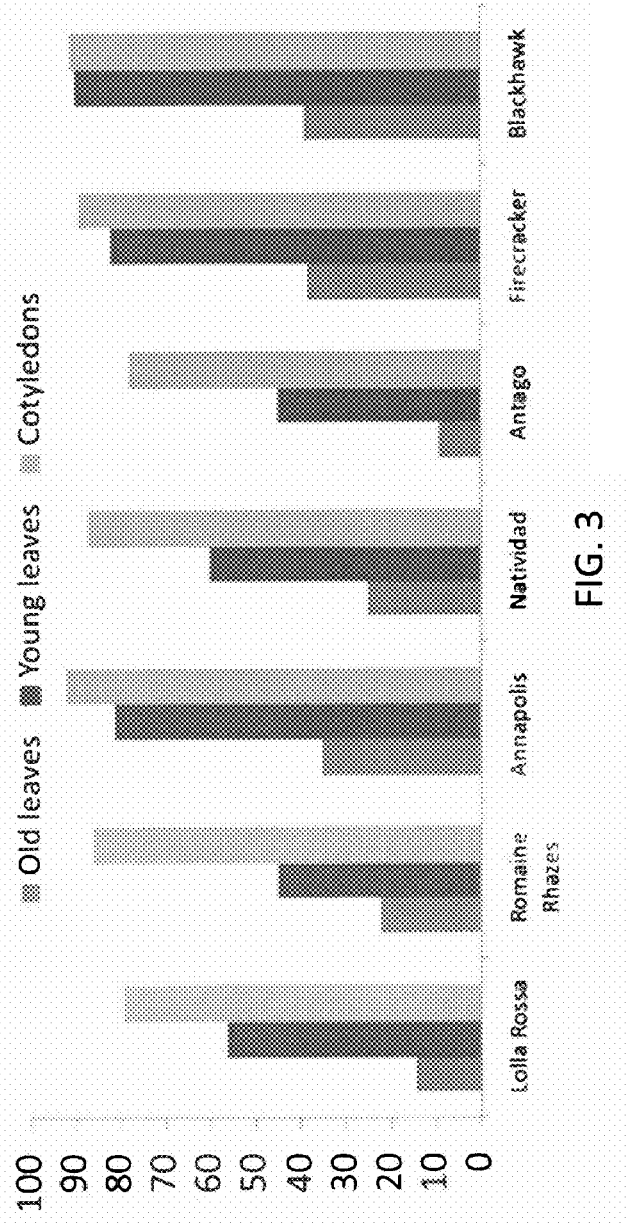
FIG. 3 is a bar graph showing shoot regeneration from different explants of lettuce.
Figure 4:
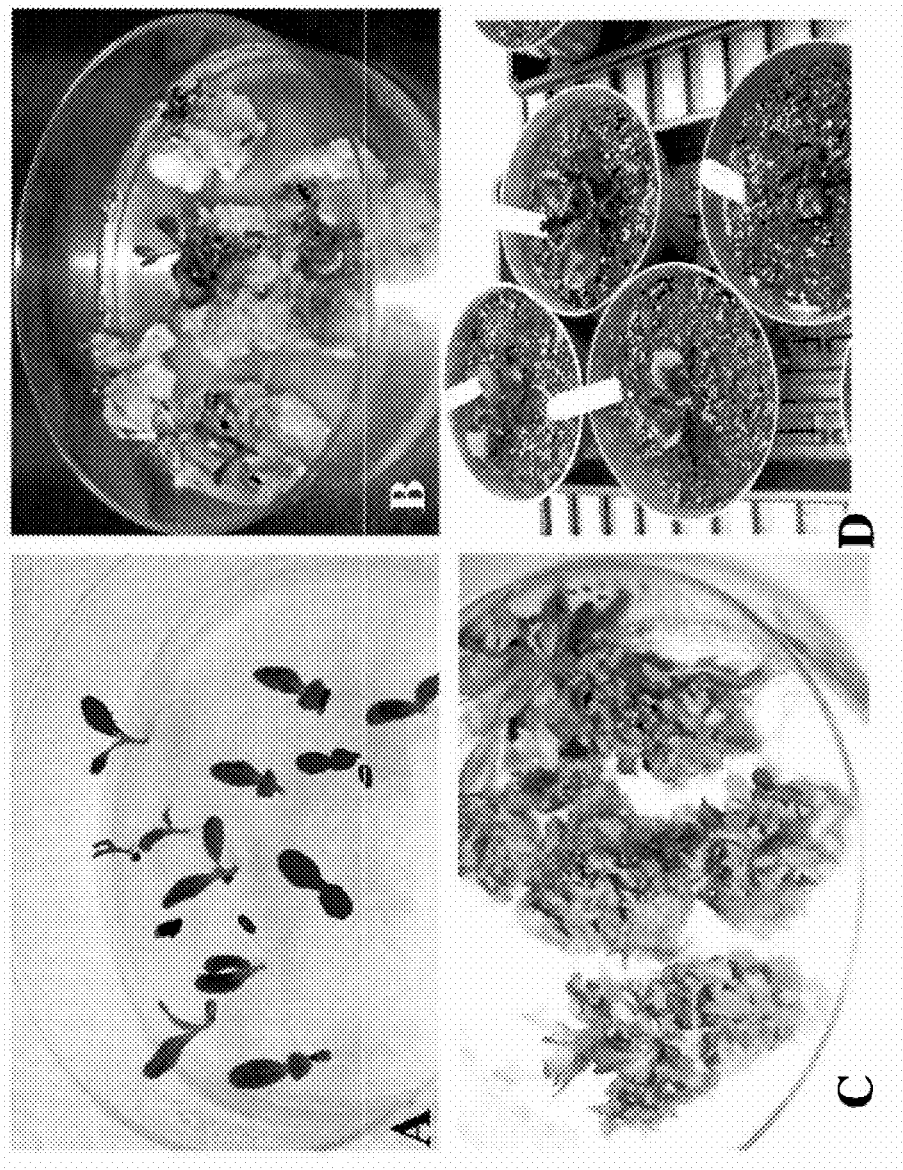
FIGS. 4A-4D are digital images showing the development of dark purple lettuce lines. (A) Cotyledons as explants for callus production, (B) shoot regeneration from callus; (C) leaves produced from callus on second regeneration medium; (D) plants produced after several regeneration cycles transferred to greenhouse.

Maximal shoot initiation was observed from the explants cultured in medium supplemented with 1 mg/l 6-benzylaminopurine (BAP), 0.5 mg/l zeatin and 0.2 mg/l NAA (R7, Table 2). During 6-7 weeks cotyledons produced multiple shoots through direct regeneration (FIGS. 2A and 2B). Comparison of regeneration capacity of six lettuce cultivars revealed the highest regeneration efficiency in Red Grand Rapids Blackhawk and Red Romaine Annapolis cotyledons, reaching 88% and 91%, respectively (FIG. 3).

Regeneration medium R7 was efficient also for young leaves; however old leaves showed very low regeneration potential. Young leaves excised from two-week old seedlings demonstrated 2-4 times higher regeneration efficiency, then old leaves from two-month-old plants. In most cases it was direct regeneration, however in some cases plants have been regenerated through an intermediate callus phase. Cultivars Red Romaine Annapolis, Red Grand Rapids Firecracker and Red Grand Rapids Blackhawk showed the greatest regeneration potential from young leaves, reaching 81%, 83% and 88%, respectively (FIG. 3). Together the data indicated that a simple, reliable protocol for high shoot regeneration from cotyledon and leaf explants of lettuce was developed.

Callus and Cell Suspensions.

Callus tissues and cell suspensions can induce a large number of somaclonal variations. It is the property of dedifferentiated cells that found application in the crop improvement and in the production of mutants and variants. For callus induction several combinations of plant hormones NAA, BAP and 2.4-D in MS medium have been used. Callus tissues were initiated from leaf explants of all seven lettuce cultivars on callus induction media after 4-6 weeks of incubation in darkness.

The highest number of callus tissues was obtained using medium MSC3. Results demonstrated that callus induction in lettuce, as well as regeneration processes, are genotype-dependent. Cultivars Red Grand Rapids Blackhawk and Dark Red Lollo Rossa produced the highest percentage of callus tissues (51-62%). For further propagation, callus tissues were transferred to MSC4 medium. After several passages on MSC4 medium fast-growing friable callus was produced for cvs Red Grang Rapids Blackhawk, Dark Red Lollo Rossa and Natividad, and used for development of cell suspension. They were growing in liquid MSCS medium supplemented with 0.5 mg/l 2.4-D.

Callus cultures and cell suspension were cultivated for 3-4 months and then transferred to regeneration medium to produce shoots. Regeneration from callus took longer than regeneration from cotyledons and leaves, in some cases up to 2.5 months. Testing of different regeneration medium demonstrated that maximum percentage of regeneration occurs on medium MSR9 that contains only cytokinins, 1 mg/l BAP and 1 mg/l zeatin.

EXAMPLE 3

Development of Somaclonal Variants

Tissue culture processes that involve dedifferentiation, long-term propagation of callus, cell suspensions, protoplasts and regeneration of plants can induce significant number of somaclonal variations (25-26, 28). In the work described herein, several methods for production of somaclonal variations have been used: several cycles of regeneration, regeneration from callus and cell suspensions, isolation of protoplasts and plant regeneration. In some experiments different combinations of these approaches were used.

Screening for Red/Purple Shoots

Several Cycles of Regeneration.

Cotyledons or young leaves have been used as explants for shoot regeneration. On regeneration medium they produced numerous shoots with wide range of color from green to red/purple. Different conditions of cultivation were evaluated including illumination source. Illumination with blue light instead of white significantly improved selection of red tissues of lettuce cultivars. The most red/purple shoots/segments were cut into pieces and placed again on the regeneration medium. When new shoots developed, they were screened for dark red/purple color and then were excised and placed on regeneration medium. Accumulation of anthocyanins was used as visual selection marker. After several rounds of regeneration and selection for dark red/purple color, 22 lines were selected. These lines were transferred for root induction and later to the greenhouse.

Regeneration from Callus and Cell Suspensions.

Callus cultures and cell suspension were cultivated for 3-4 months and then transferred to regeneration medium to produce shoots. Regeneration process from callus was more difficult and took longer than regeneration from cotyledons and leaves, in some cases up to 2.5 months. Some callus tissues developed clear visible red sectors, and shoot-like structures. The maximum percentage of regeneration from callus occurs on medium R9 that contains only cytokinins, particularly 1 mg/l BAP and 1 mg/l zeatin. Shoots regenerated from callus were screened for dark red/purple color and in some cases used for several cycles of regeneration (FIGS. 4A-4D). 15 lines were produced from Red Grand Rapids Blackhawk, Red Romaine Annapolis, and Red Grand Rapids Firecracker cultivars.

Plant Regeneration from Protoplasts.

For protoplast isolation, young leaves from shoot cultures have been used. Protoplasts isolation and purification was performed according to the protocols previously described (19) with minor modifications. The digestion medium supplemented with 0.5% cellulose RS and 1.5% macerozyme R10 showed the best results for lettuce. After 16 hours of this treatment, the majority of protoplasts were isolated, some of which had a distinct red color. After washing protoplasts, they were cultivated in liquid MO2 medium with for 2 weeks, then transferred into medium with reduced osmotic pressure. Protoplasts plated in MO2 medium formed cell wall readily, and divided within six to eight days of culture. After 1.5 month numerous large cell colonies developed. Shoot regeneration was induced on the MS medium containing 1 mg/l BAP and 0.1 mg/l NAA. After selection for red color, 9 red shoots were rooted onto MS medium, and transferred to greenhouse.

Chemical Mutagenesis of Seeds

Induced mutation can broaden genetic variants and provide materials for plant improvement. Lettuce seeds from the original starting varieties were used for mutagenic treatment with EMS and NMU (24). After mutagenic treatment and surface sterilization, seeds were germinated. Cotyledons were excised and transferred for regeneration medium. Numerous shoots were produced on regeneration medium, and several had red color. After several rounds of regeneration, dark red variants were produced. The greater yield of dark red shoots appeared from EMS-mutagenized seeds. 17 lines were produced after chemical treatment and transferred to greenhouse.

UV Treatment of Leaves and Callus Tissues.

Shoot cultures growing in vitro conditions were treated by UV-A. Treatment was repeated 8 times. However, lettuce leaves are very sensitive and some of them were significantly damaged after treatment. Surviving young leaves were cut into pieces and placed onto regeneration medium for selection of red shoots. In other experiments, callus tissues were treated by UV-A for 20 min, and treatment repeated 8 times. Callus tissues were transferred to regeneration medium and after 7-8 weeks, regenerants were produced. 11 lines were produced and transferred to greenhouse.

EXAMPLE 5

Phytochemical Analyses of Control and New Lettuce Varieties

Sample Extraction

High-quality leaf samples were selected and harvested from greenhouse grown plants. Lettuce leaves were harvested after 70 days of growth. Fresh weights were recorded and leaves were frozen at $-80°$ C. prior to lyophilization. Dry weights were recorded and leaves were ground to a fine powder with a mortar and pestle. Sample extracts were prepared as described by Wu et al. (*J Agric Food Chem*, 52:4026-4037, 2004) with slight modifications. Briefly, 0.5 g of dried material was transferred to a 50 mL protected from light and 15 mL of extraction solvent (methanol/$H_2$O/acetic acid; 85:14.5:0.5) was added. Samples were vortexed for 30 seconds, sonicated for 5 min, vortexed for 30 seconds, then incubated at room temperature for 10 min. Samples were vortexed for 5 seconds then centrifuged at 4000 rpm (1699 rcf) for 5 minutes. The supernatant was decanted and the extraction process was repeated two more times. The supernatants were pooled (45 mL) and filtered through 0.45 μm PTFE filters (VWR International, Radnor, Pa.) prior to analyses. Samples were stored at $-20°$ C.

Phytochemical Analyses

Total Phenolics

Total phenolic content was measured by a modified Folin-Ciocalteu method (36, 37) Folin-Ciocalteu phenol reagent (Sigma) was combined with 50% methanol (1:1). The 1N Folin-Ciocalteu reagent was added to 200 μL of diluted sample and incubated at room temperature for 10 min. Next, 300 μL 2M $Na_2CO_3$ was added, mixed by vortexing, and incubated in a $40°$ C. water bath for 20 minutes. Samples were cooled on ice and centrifuged for 30 seconds at 7000 rcf. The supernatant was transferred to a 96-well plate and absorbance was measured at 760 nm in triplicate on a Synergy HT Multi-Detection Microplate Reader (Bio-Tek, Winooski, Vt.). Gallic acid (Sigma) was used to generate a linear calibration curve and results were expressed as gallic acid equivalents.

Anthocyanins

Total monomeric anthocyanin content was determined according to the AOAC pH differential method (31, 33). Samples were diluted as needed and pH 1 (25 mM potassium chloride) and pH 4.5 buffers (0.4 M sodium acetate) were added to each sample. Absorbances of the pH 1 and pH 4.5 solutions were measured at 510 nm and 700 nm in a Synergy HT Multi-Detection Microplate Reader (Bio-Tek, Winooski, Vt.) in triplicate. Anthocyanin content was calculated according to the AOAC protocol and expressed as cyanidin-3-glucoside equivalents.

Characterization of Polyphenolics in Red Lettuce by Matrix-Assisted Laser Desorption/Ionization Time-of-Flight Time-of-Flight Mass Spectrometry (MALDI-TOF-TOF MS)

Analysis of two new lettuce varieties (NBR-S-16, NFR-S-4) phenolics were performed by analytic high performance liquid chromatography (HPLC). The analytes (0.5 g)

were subjected to ultrasonic extraction (10 minutes) in an aqueous organic solvent [50% aq. MeOH (0.5% acetic Acid); 15 ml], centrifuged (1900G) and the supernatant was decanted. This process was repeated three times. Supernatants were combined and equilibrated to 50 ml (volumetric flask) before being injected (100 µl) onto a C-18 column (Waters ODS-2, 25 cm×0.45 cm). The solvents for elution were 0.1% trifluoroacetic acid in water (solvent A) and methanol (solvent B). A step gradient program was developed that optimized the separation of phenolics. The program was 90% A to 72% A over 10 min under a linear gradient, isocratic for 20 min, 72% A to 45% A over the next 20 min under linear gradient, then 100% solvent B over the next 5 min with a linear gradient. Waters Empower software was used to generate a 3-dimensional (3D) data set (absorbance, retention time, and wavelength) for the analyte and calibration standards.

Mass spectra were collected on a Bruker ULTRAFLEX®III MALDI TOF/TOF mass spectrometer (Billerica, Mass., USA) equipped with delayed extraction and a SmartBeam® laser. All analyses were performed in positive reflectron mode. Spectra were the sum of 8-10 different locations in each well, accumulating a total of 400-500 shots to minimize intra-well variability and avoid heterogeneous co-crystallization spots. Threshold laser power was used to achieve optimal isotope patterns. The matrix was 2,5-dihydroxybenzoic acid (DHB) at a concentration of 50.0 mg/mL in ethanol. FlexControl and FlexAnalysis (Bruker Daltonik GmbH, Bremen, Germany, version 3.0) were used for data acquisition and data processing, respectively. mMass (version 3.9.0) was used for spectra analysis. Identities of the peaks were confirmed with analytical standards.

Oxygen Radical Absorption Capacity Assay

Oxygen radical absorption capacity was measured as described (32, 35) with slight modifications. Trolox® ((±)-6-Hydroxy-2,5,7,8-tetramethylchromane-2-carboxylic acid, 97%), fluorescein sodium salt, AAPH (2,2'-Azobis(2-methylpropionamidine) dihydrochloride), and phosphate buffered saline 10× concentrate were purchased from Sigma. All reagents and sample dilutions were made in 75 mM PBS, pH 7. Stock solutions of fluorescein 1 mM and Trolox 2.5 mM were prepared and single use aliquots were stored at −20° C. Water was pipetted into the outer wells of a 96-well plate. Fluorescein was diluted to 6 nM from the stock solution and 150 µl of was added to each well. Next, 25 µl of Trolox standard (50, 25, 12.5, 6.25, 3.125 µM) and samples were added to each well in triplicate. The plate was preincubated at 37° C. for 30 min. A fresh solution of AAPH 127 mM was prepared and 25 µL added to each well after preincubation.

Fluorescence readings were recorded every minute for 75 minutes with a 485 nm, 20 nm bandpass, excitation filter and a 528 nm, 20 nm bandpass, emission filter in a Synergy HT Multi-Detection Microplate Reader (Bio-Tek, Winooski, Vt.). The area under the curve (AUC) was calculated by the equation: $0.5 + R2/R1 + R3/R1 + \ldots + R75/R1 + R76/R1 * 0.5$, where R1 is the first reading, R2 is the second reading etc. The net AUC was calculated by subtracting the AUC of the blank from the standard or sample. A regression line was generated by plotting the concentration of Trolox by net AUC. The regression equation was used to calculate µM Trolox equivalents. Results were expressed as µmol Trolox equivalents per g fresh weight for each sample.

Results

Control.

Original (control) lettuce cultivars (cvs. Red Lollo Natividad, Red Grand Rapids Firecracker, Dark Red Lollo Rossa, Antago, Red Grand Rapids Blackhawk, Red Romaine Annapolis, and Red Romaine Rhazes) were investigated in greenhouse conditions. They were grown hydroponically in greenhouse at 16-h light/8-h dark photoperiod. All cultivars, in general, look green with some areas of red color, in most cases the red is at the ends of leaves and around veins. Most red coloration had cv. Red Lollo Antago. All cultivars were grown in the greenhouse until the age of 9-10 weeks, after which the plants were harvested. These plants were tested for level of total polyphenols and anthocyanins. All control plants had low levels of total polyphenols and anthocyanins (Table 3).

TABLE 3

Phytonutrient and oxygen radical absorption capacity (ORAC) of lettuces and blueberry. Phenolic content, anthocyanin content, and ORAC are expressed as gallic acid, cyanidin-3-glucoside and trolox equivalents, per gram fresh weight (FW), respectively.

| Source | Cultivar | Color | Phytonutrient | (mg/g fresh weight (FW)) | ORAC (µmol/g FW) |
|---|---|---|---|---|---|
| Lettuce NFR-S-4 | Red Grand Rapids Firecracker | Red | Phenolics Anthocyanins | 9.96 2.06 | 273 |
| Lettuce S-13 | Annapolis | Red | Phenolics Anthocyanins | 10.88 2.41 | 267 |
| Lettuce NBR-S-16 | Red Grand Rapids Blackhawk | Red | Phenolics Anthocyanins | 8.60 1.91 | 253 |
| Lettuce NRR-S-21 | Dark Red Lollo Rossa | Red | Phenolics Anthocyanins | 7.17 1.13 | 210 |
| Lettuce | Red Romaine Annapolis | Green | Phenolics Anthocyanins | 0.73 0.00 | 18 |
| Lettuce | Red Grand Rapids Firecracker | Green | Phenolics Anthocyanins | 2.28 0.88 | 104 |
| Lettuce | Red Grand Rapids Blackhawk | Green | Phenolics Anthocyanins | 2.14 0.20 | 91 |
| Lettuce | Dark Red Lollo Rossa | Green | Phenolics Anthocyanins | 1.08 0.00 | 111 |
| Lettuce | Romaine (Commercial) | Green | Phenolics Anthocyanins | 0.82 0 | 40 |
| Lettuce | Boston (Commercial) | Green | Phenolics Anthocyanins | 0.05 0 | 13 |
| Lettuce | Leaf (Commercial) | Green | Phenolics Anthocyanins | 1.67 0 | 47 |
| Blueberry | Highbush (Commercial) | | Phenolics Anthocyanins | 2.94 1.30 | 66 |
| Lettuce | (Llorach et al., 2008 Food Chem; Li et al., 2010 J Agric Food Chem) | Red | Phenolics Anthocyanins | 5.70 0.50 | 7 |
| Blueberry | Highbush (Prior et al., 1998 J Agric Food Chem) | | Phenolics Anthocyanins | 2.61 1.30 | 24 |

Somaclonal Variants and Mutants.

Figure 5:
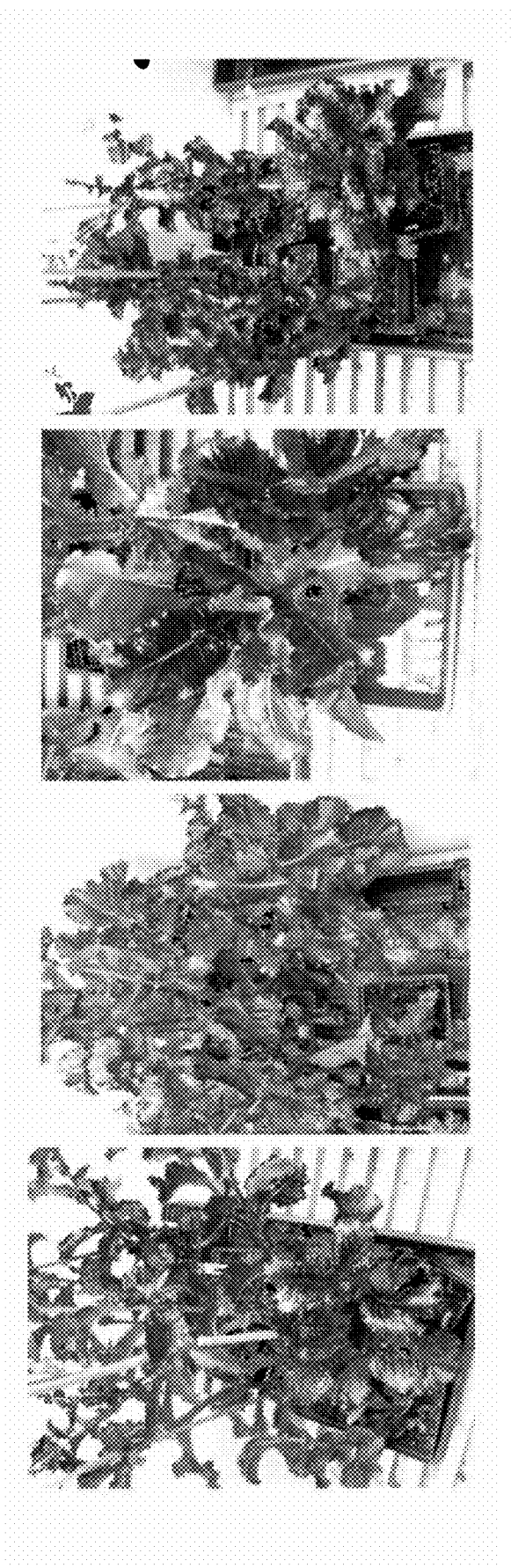
FIG. 5 is a digital image showing plants produced by tissue culture and mutagenesis growing in a greenhouse for seed production.

After all tissue culture experiments and mutagenic treatment, 74 lines were produced. All were transferred to greenhouse. Several lines demonstrated intensive dark red or purple color (FIG. 5). Seeds were produced from all red lettuce lines after self-pollination. Seeds were germinated in greenhouse conditions and F1 plants produced. Most dark red plants from F1 progeny were analyzed (FIGS. 6A-6G). Results of showed that lines produced in tissue culture contain extremely high amounts of total polyphenols and anthocyanins (Table 3). As shown in Table 4, several major polyphenols were present in the new varieties described herein.

TABLE 4

Biochemical analysis of major polyphenols in two new red lettuce varieties

| | mg/g Dry Weight (DW) | | |
|---|---|---|---|
| Polyphenol Class | NBR-S-16 | NFR-S-4 | S-13 |
| Chlorogenic acid | 27.6 | 23.9 | 26.8 |
| Quercetin 3 glucoside | 9.9 | 13.1 | 8.7 |
| Quercetin malonylglucoside | 31.9 | 35.7 | 30.9 |
| Cyanidin malonylglucoside | 17.0 | 20.5 | 18.3 |

EXAMPLE 6

Effect of New Lettuce Varieties on Blood Glucose Levels In Vivo

This example describes methods used to demonstrate that the disclosed lettuce varieties can be used to reduce blood glucose levels.

Methods

Five-week-old male C57Bl/6J mice (Jackson Labs) were housed in cages (five mice to a cage) at 25° C. with 12-h light-dark cycle. Mice were given ad libitum access to food and water and after an acclimatization period of one week, rodent diet was switched from chow (Purina, No. 5015) to a very high fat diet (VHFD) containing 60% kcal fat (D12492, Research Diets, New Brunswick, N.J.) for a at least 12 weeks to induce obesity, insulin resistance, and hyperglycemia (Surwit et al., *Clin. Exp. Met.*, 44:645-51, 1995). Weekly food intake per cage and individual body weight measurements were determined throughout the study. All mice were introduced to intragastric feeding prior to treatment. During this time, a gavage administration of 0.2 mL of double distilled water was performed daily for 2-3 days prior to the scheduled experiments.

For all experiments, mice were randomly divided into fasting blood glucose (FBG)-balanced experimental groups. Lettuce leaves were lyophilized powdered and suspended in 66% labrasol or water for the aqueous extract and Metformin® antidiabetic drug was dissolved in water. Blood glucose levels were measured using an AlphaTrak® hand-held glucometer (Abbott Labs Inc., Abbott Park, Ill.) using test strips.

In experiment 1, following a 4 hour fasting period, FBG was measured immediately prior to treatment and 6 hours post treatment. Mice were treated using an oral ingestion of vehicle (66% labrasol, Gattefosse, Cedex, France), NFR-S-4 (25, 50, or 100 mg/kg), or Metformin® antidiabetic drug (300 mg/kg, Sigma) (n=4-5) (Table 5).

In experiment 2, high fat diet-induced obese mice, animals were given daily oral administration of NFR-S-4 aqueous extract (100 or 300 mg/kg) or vehicle (water) for 28 days (n=10) (Table 6). A Metformin® antidiabetic drug group (250 mg/kg) was included as a positive control for the animal model (n=5). Aqueous extracts were prepared by a 5:1 extraction (solvent volume to fresh weight) in hot (100° C.) acidified water (pH 2 with $H_2SO_4$) to assist with anthocyanin stability during the extraction process. Mice were fasted overnight prior to an oral glucose tolerance test. For oral glucose tolerance tests, mice were given an oral glucose challenge (2 g/kg) and blood glucose levels were measured prior to glucose challenge and 30, 60, 90, 120 and 180 minutes after glucose administration (Table 6).

In experiment 3, mice were treated using an oral ingestion of vehicle (66% labrasol), S-13 lettuce (100, 300 or 450 mg/kg), green Romaine lettuce (450 mg/kg, commercially available), or Metformin® antidiabetic drug (300 mg/kg) (n=4-5 Following a 4 h fasting period, FBG was measured immediately prior to treatment and 6 h post treatment (Table 7).

In experiment 4, mice were treated with S-13 lettuce (100 mg/kg), vehicle (66% labrasol), or Metformin® antidiabetic drug (300 mg/kg) by oral administration (n=8-10). After 2 h, mice were given an oral glucose tolerance test as described above (Table 8).

Statistical Analysis

Statistically significant differences between were analyzed by ANOVA followed by Dunnett's multiple comparisons test and/or paired t-tests (one tail) comparing FBG levels immediately prior to treatment (0 h) and 6 hours after treatment (Table 5). A p-value <0.05 was considered statistically significant.

Results

As shown in Tables 5 and 7, mice having diet induced obese hyperglycemia who received NFR-S-4 or S-13 lettuce saw a reduction in fasting blood glucose.

As shown in Tables 6 and 8, NFR-S-4 aqueous extract and S-13 lyophilized leaves improved glucose metabolism measured by oral glucose tolerance tests. After 25 d of NFR-S-4 extract treatment (100 and 300 mg/kg) had significantly lower AUC compared to vehicle (water) control group. Similarly, acute treatment with S-13 lyophilized leaves had significantly lower AUC compared to vehicle (labrasol) control group

TABLE 5

Reduction in fasting blood glucose in diet induced obese hyperglycemic mice administered NFR-S-4 lettuce. Fasting blood glucose (FBG) levels are presented as mean +/− standard deviation.

| | Vehicle | NFR-S-4 25 mg/kg | NFR-S-4 50 mg/kg | NFR-S-4 100 mg/kg | Metformin ® drug 300 mg/kg |
|---|---|---|---|---|---|
| FBG (mg/dL) | | | | | |
| 0 h | 224 +/− 13 | 221 +/− 29 | 221 +/− 26 | 228 +/− 29 | 222 +/− 19 |
| 6 h | 220 +/− 53 | 200 +/− 13 | 190 +/− 37 | 162 +/− 13 | 133 +/− 25 |
| % Decrease | 2 +/− 19 | 8 +/− 16 | 14 +/− 14 | 29 +/− 7 | 39 +/− 14 |
| p-value | 0.4422 | 0.1202 | 0.0484 | 0.0014 | 0.0026 |
| n | 4 | 5 | 5 | 5 | 5 |

TABLE 6

Oral glucose tolerance test. Improved glucose metabolism of diet induced obese hyperglycemic mice administered lettuce NFR S-4 aqueous extract for 25 days compared to vehicle (water). Fasting blood glucose (FBG) levels are presented as mean +/- standard deviation.

|  | Time (min) | | | | | Area under the curve | n |
|---|---|---|---|---|---|---|---|
|  | 0 | 30 | 60 | 90 | 120 | | |
| FBG (mg/dL) | | | | | | | |
| Vehicle | 260 +/- 26 | 408 +/- 65 | 337 +/- 71 | 303 +/- 63 | 270 +/- 56 | 39386 | 10 |
| NFR-S-4 (300 mg/kg) | 224 +/- 24 | 286 +/- 50 | 299 +/- 56 | 276 +/- 35 | 268 +/- 49 | 33231 | 10 |
| NFR-S-4 (100 mg/kg) | 224 +/- 37 | 339 +/- 55 | 277 +/- 31 | 267 +/- 51 | 241 +/- 29 | 33471 | 10 |
| Metformin (250 mg/kg) | 181 +/- 26 | 298 +/- 52 | 244 +/- 19 | 247 +/- 32 | 249 +/- 35 | 30153 | 5 |
| p-value (vs. Vehicle) | | | | | | | |
| NFR-S-4 (300 mg/kg) | 0.0030 | 0.0001 | 0.1000 | 0.1320 | 0.4633 | 0.0029 | |
| NFR-S-4 (100 mg/kg) | 0.0116 | 0.0097 | 0.0121 | 0.0935 | 0.0862 | 0.0040 | |
| Metformin (250 mg/kg) | 0.0001 | 0.0031 | 0.0072 | 0.0461 | 0.2340 | 0.0019 | |

TABLE 7

Reduction in fasting blood glucose in diet induced obese hyperglycemic mice treated with S-13. Fasting blood glucose (FBG) levels are presented as mean +/- standard deviation.

|  | Vehicle | Metformin ® 300 mg/kg | S-13 100 mg/kg | S-13 300 mg/kg | S-13 450 mg/kg | Green Romaine lettuce 450 mg/kg |
|---|---|---|---|---|---|---|
| FBG (mg/dL) | | | | | | |
| 0 | 264 +/- 38 | 214 +/- 20 | 258 +/- 50 | 269 +/- 28 | 258 +/- 43 | 255 +/- 17 |
| 6 h | 233 +/- 32 | 146 +/- 34 | 183 +/- 44 | 177 +/- 24 | 172 +/- 30 | 215 +/- 9 |
| % Decrease | 0.1 +/- 17 | 31 +/- 19 | 24 +/- 19 | 26 +/- 9 | 29 +/- 15 | 1.6 +/- 5 |
| p-value | 0.4660 | 0.0314 | 0.0249 | 0.0038 | 0.0155 | 0.2229 |
| n | 5 | 4 | 5 | 5 | 5 | 5 |

TABLE 8

Oral glucose tolerance test. Improved glucose metabolism of diet induced obese hyperglycemic mice administered lettuce S-13. Fasting blood glucose (FBG) levels are presented as mean +/- standard deviation.

|  | Time (min) | | | | | | Area under the curve | n |
|---|---|---|---|---|---|---|---|---|
|  | 0 | 30 | 60 | 90 | 120 | 180 | | |
| FBG (mg/dL) | | | | | | | | |
| Vehicle | 225 +/- 62 | 379 +/- 55 | 332 +/- 44 | 319 +/- 46 | 226 +/- 29 | 193 +/- 27 | 50235 | 10 |
| S-13 (100 mg/kg) | 209 +/- 44 | 272 +/- 72 | 243 +/- 50 | 222 +/- 44 | 210 +/- 70 | 166 +/- 32 | 39677 | 9 |

TABLE 8-continued

Oral glucose tolerance test. Improved glucose metabolism of diet induced obese hyperglycemic mice administered lettuce S-13. Fasting blood glucose (FBG) levels are presented as mean +/- standard deviation.

| | Time (min) | | | | | | Area under the curve | n |
|---|---|---|---|---|---|---|---|---|
| | 0 | 30 | 60 | 90 | 120 | 180 | | |
| Metformin® (300 mg/kg) | 206 +/- 45 | 261 +/- 51 | 263 +/- 69 | 257 +/- 62 | 196 +/- 31 | 176 +/- 30 | 40683 | 8 |
| p-value (vs Vehicle) | | | | | | | | |
| S-13 (100 mg/kg) | 0.2644 | 0.0010 | 0.0004 | 0.0001 | 0.2586 | 0.0317 | 0.0007 | |
| Metformin® (300 mg/kg) | 0.2379 | 0.0001 | 0.0106 | 0.0134 | 0.0269 | 0.1143 | 0.0031 | |

REFERENCES

1. Seeram et al., (2004) Total cranberry extract versus its phytochemical constituents: antiproliferative and synergistic effects against human cancer cell lines. *J. Agric. Food Chem.* 52:2512-7
2. Renaud, S. & Lorgeril, M. (1992) Wine, alcohol, platelets, and the French paradox for coronary heart disease. *Lancet* 339:1523-6
3. Ness A. R., Powles J. W. 1997 Fruit and vegetables, and cardiovascular disease: a review. *Int. J. Epidemiol.* 26: 1-13
4. Hou et al., (2004) Molecular mechanisms behind the chemopreventive effects of anthocyanidins. *J. Biomed. Biotechnol.,* 5:321-325
5. Joseph et al., (1999) Reversals of age-related declines in neuronal signal transduction, cognitive, motor behavioral deficits with blueberry, spinach, or strawberry dietary supplementation. *J. Neurosci.:* 19, 8114-8121
6. Shin et al., (2006) Protective effect of anthocyanins in middle cerebral artery occlusion and reperfusion model of cerebral ischemia in rats. *Life Sci.,* 79, 130-137
7. Lila M. A. (2004) Anthocyanins and human health: an in vitro investigative approach. *J. Biomed. Biotechnol.* 5:306-313
8. Tsuda et al., (2003) Dietary cyanidin 3-O-beta-glucoside-rich purple corn color prevents obesity and ameliorates hyperglycemia in mice, *J. Nutr.* 133:2125-2130
9. Economic Research Service, U.S. Dept. of Agriculture, Loss-Adjusted food availability data, Vegetables, 2011, www.ers.usda.gov/Data/FoodConsumption/FoodGuideIndex.htm#veg.
10. Gao, L. & Mazza, G. (1994) Quantitation and distribution of simple and acylated anthocyanins and other phenolics in blueberries. J. Food Sci. 59(5): 1057-1059.
11. Gazula et al., (2007) Anthocyanin levels in nine lettuce (*Lactuca sativa*) cultivars: influence of plating date and relations among analytic, instrumented, and visual assessments of color. HortScience, 42 (2):232-238
12. Llorach et al., (2008) Characterization of polyphenols and antioxidant properties of five lettuce varieties and escarole. Food Chemistry, 108, 1028-1038.
13. Boo et al., (2011) Positive effects of temperature and growth conditions on enzymatic and antioxidant status in lettuce plants. *Plant Sci.,* 181:479-484.
14. Chon et al., (2012) Anthocyanin content and the activities of polyphenol oxidaxe, peroxidase and phenylalanine ammonia-lyase in lettuce cultivars. *International Journal of Food Sciences and Nutrition,* 63(1):45-48.
15. Li et al., (2010). Effects of exogenous abscisic acid on yield, antioxidant capacities, and phytochemical contents of greenhouse grown lettuces. *J. Agric. Food Chem.,* 26, 58 (10), 6503-6509.
16. Volpio, I. & Autio, J (1995) Responses of red-leaved lettuce to light intensity, UV-A radiation and root zone temperature. *Acta Horticulturae* 399:183-187.
17. Kleinhenz et al (2003) Variety, shading, and growth stage effects on pigment concentrations in lettuce grown under contrasting temperature regimes. Horticulture 13(4), p. 677-683
18. Murashige & Skoog (1962) A revised medium for rapid growth and bioassays with tobacco tissue cultures. Physiol. Plant. 15:473-497
19. Gleba et al., (1982). Intertribal hybrid cell lines of *Atropa belladonna+Nicotiana chinensis* obtained by cloning individual protoplasts fusion products. *Theor. Appl. Genet.* 62:75-79
20. Kushnir et al., (1987) Functional cybrid plants possessing a *Nicotiana* genome and *Atropa* plastome. *Mol Gen Genet.,* 209:159-163
21. Pogrebnyak et al., (1992) Herbicide-resistant mutant cell lines and plants of potato. Cytology and Genetics, 26, N2, 50-55.
22. Xinrun, Z., Conner, A. J. (1992) Genotypic effects on tissue culture response of lettuce cotyledons. *J. Genet. Breed.* 46, 287-290
23. Mohebodini et al., (2011). Effects of genotype, explants age and growth regulators on callus induction and direct shoot regeneration of lettuce (*Lactuca sativa* L.), *Australian J Crop Science,* 5(1):92-95.
24. Greene et al., (2003) Spectrum of chemically induced mutations from a large-scale reverse-genetic screen in *Arabidopsis. Genetics* 164:731-740.
25. Karp and Bright, (1985) On the causes and origins of somaclonal variation. Oxford Surveys of Plant Mil Cell Biol 2:199-234.
26. Shuahgxia et al., (2008). Detection of somaclonal variation of cotton (*Gossypium hirsutum*) using cytogenetics, flow cytometry and molecular markers. Plant Cell Rep 27(8): 1303-16.
27. Brown D. C. W. & Thorpe T. A. (1995) Crop improvement through tissue culture. *World Journal of Microbiology and Biotechnology,* 11, 409-415.

28. Larkin P. J. & Scowcroft, W. R. (1981) Somaclonal variation—a novel source of variability from cell culture for plant improvement. *Theoret. Appl. Genet.*, 60:197-214
29. Ampomah-Dwamena, C., Conner, A. J., Fautrier, A. G. (1997) Genotypic response of lettuce cotyledons to regeneration in vitro. Scientia Horticulturae, 71, 137-145.
30. Hunter, D. C., Burritt, D. J. (2002) Improved adventitious shoot production from cotyledon explants of lettuce (*Lactuca sativa* L.) Scientia Horticulturae, 95, 269-276.
31. AOAC Official Method 2005.02 2005, "Total monomeric anthocyanin pigment content of fruit juices, beverages, natural colorants, and wines", *J. AOAC Int.*, vol. 88, pp. 1269-1270.
32. Held, P. 2005, "Performing oxygen radical absorbance capacity (ORAC) assays with Synergy™ HT Multi-Mode Microplate Reader-ORAC antioxidant tests", www.biotek.com/resources/articles/performing-orac-assays.html
33. Prior et al., 1998, "Antioxidant capacity as influenced by total phenolic and anthocyanin content, maturity, and variety of *Vaccinium* species", *J. Agric. Food Chem.*, 46:2686-93.
34. Prior et al., 2010, "Multi-laboratory validation of a standard method for quantifying proanthocyanidins in cranberry powders", *Journal of the Science of Food and Agriculture*, vol. 90, pp. 1473-1478.
35. Prior et al., 2003, "Assays for hydrophilic and lipophilic antioxidant capacity (oxygen radical absorbance capacity (ORAC(FL))) of plasma and other biological and food samples", *J Agric Food Chem*, vol. 51, pp. 3273-3279.
36. Sharma et al., 2010, "Effects of fruit ellagitannin extracts, ellagic acid, and their colonic metabolite, urolithin A, on Wnt signaling", *Journal of Agricultural and Food Chemistry*, vol. 58, no. 7, pp. 3965-3969.
37. Singleton et al., 1999, "Analysis of total phenols and other oxidation substrates and antioxidants by means of Folin-Ciocalteu reagent" in *Methods in Enzymology*, ed. L. Packer, Academic Press, New York, pp. 152-178.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A lettuce seed deposited under ATCC Accession No. PTA-120680, PTA-120681 or PTA-120682.

2. A seed mixture, comprising the seed of claim 1.

3. A lettuce plant produced by growing the seed of claim 1.

4. An $F_1$ lettuce seed produced from the lettuce plant of claim 3.

5. A plant part from the lettuce plant of claim 3.

6. The plant part of claim 5, wherein the part is a head, a lettuce leaf, part of a lettuce leaf, pollen, ovule, or flower.

7. A tissue culture produced from protoplasts or cells from the lettuce plant of claim 3.

8. A lettuce plant regenerated from the tissue culture of claim 7, wherein the regenerated lettuce plant has:
   at least 1.1 mg/g fresh weight (FW) anthocyanins;
   at least 5 mg/g FW phenolics;
   at least 100 µmol/g FW oxygen radical absorption capacity;
   at least 10 mg/g dry weight (DW) chlorogenic acid;
   at least 4 mg/g DW dicaffeoylquinic acid;
   at least 12 mg/g DW quercetin malonylglucoside;
   at least 7 mg/g DW cyanidin malonylglucoside; or
   combinations thereof.

9. A plant part from the plant of claim 8.

10. A tissue culture produced from protoplasts or cells from the lettuce plant of claim 8.

11. A lettuce plant regenerated from the tissue culture of claim 10.

12. An $F_1$ hybrid lettuce plant having the lettuce plant of claim 3 as a parent.

13. Pollen or an ovule of the lettuce plant of claim 3.

14. A salad mix comprising leaves of the plant of claim 3.

15. A method of producing the lettuce plant of claim 3 comprising an added desired trait, comprising:
   introducing a transgene conferring the desired trait into the lettuce plant of claim 3, thereby producing the lettuce plant of claim 3 comprising the added desired trait.

16. The method of claim 15, wherein the transgene further comprises one or more expression control sequences.

17. A lettuce plant produced by the method of claim 15.

18. The method of claim 15, wherein the desired trait is one or more of herbicide tolerance or resistance, drought tolerance, heat tolerance, low or high soil pH level tolerance, salt tolerance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination, abiotic stress tolerance, modified antioxidant characteristics, modified anthocyanins, or modified polyphenols characteristics.

19. The method of claim 18, wherein the herbicide resistance comprises tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, and chlorophenoxy acetic acid.

20. The method of claim 18, wherein insect resistance is conferred by a transgene encoding a *Bacillus thuringiensis* (Bt) endotoxin.

21. A method of introducing a desired trait into the lettuce plant of claim 3, comprising:
   (a) crossing the plant of claim 3 with a second lettuce plant comprising a desired trait to produce $F_1$ progeny plants;
   (b) selecting $F_1$ progeny plants that have the desired trait to produce selected $F_1$ progeny plants;
   (c) crossing the selected progeny plants with at least a first plant of claim 3 to produce backcross progeny plants;
   (d) selecting backcross progeny plants that have the desired trait and physiological and morphological characteristics of the lettuce plant of claim 3 to produce selected backcross progeny plants; and
   (e) repeating steps (c) and (d) one or more times in succession to produce selected second or higher backcross progeny plants that comprise the desired trait and the physiological and morphological characteristics of the lettuce plant of claim 3 when grown in the same environmental conditions.

22. A lettuce seed deposited under ATCC Accession No. PTA-120680, PTA-120681 or PTA-120682, further comprising a single locus conversion.

23. A method of producing an inbred lettuce plant derived from the lettuce plant of claim 3, comprising:
   (a) preparing a progeny plant derived from the lettuce plant of claim 3 by crossing a plant of the lettuce plant of claim 3 with a lettuce plant of a second variety;

(b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional 3-10 generations with sufficient inbreeding to produce an inbred lettuce plant derived the lettuce plant of claim 3.

24. A method of making lettuce seeds, comprising, crossing the plant of claim 3 with another lettuce plant; and harvesting seed therefrom.

25. A method of making an extract, comprising:

(a) grinding frozen leaves of the plant of claim 3 to generate a powder; or (b) macerating leaves of the plant of claim 3 and exposing the macerated leaves to an extraction solvent;

thereby generating the extract.

26. A method of decreasing blood glucose in a subject, comprising:

administering the plant of claim 3 to a subject; and decreasing the blood glucose level in the subject.

\* \* \* \* \*